US012807917B2

(12) United States Patent
Rzasa et al.

(10) Patent No.: US 12,807,917 B2
(45) Date of Patent: Nov. 24, 2026

(54) SYSTEMS, DEVICES, AND METHODS FOR CLOSED-LOOP BIOELECTRONIC CONTROL

(71) Applicant: University of Maryland, College Park, College Park, MD (US)

(72) Inventors: John Robertson Rzasa, University Park, MD (US); Sally Wang, Greenbelt, MD (US); Chen-Yu Chen, Beltsville, MD (US); Chen-Yu Tsao, Potomac, MD (US); William E. Bentley, Annapolis, MD (US)

(73) Assignee: UNIVERSITY OF MARYLAND, COLLEGE PARK, College Park, MD (US)

(*) Notice: Subject to any disclaimer, the term of this patent is extended or adjusted under 35 U.S.C. 154(b) by 782 days.

(21) Appl. No.: 18/300,941

(22) Filed: Apr. 14, 2023

(65) Prior Publication Data

US 2023/0332087 A1 Oct. 19, 2023

Related U.S. Application Data

(60) Provisional application No. 63/363,004, filed on Apr. 14, 2022.

(51) Int. Cl.

*C12M 1/42* (2006.01)
*C12M 1/32* (2006.01)
(Continued)

(52) U.S. Cl.

CPC ............ *C12M 35/02* (2013.01); *C12M 23/12* (2013.01); *C12M 41/46* (2013.01); *C12M 41/48* (2013.01);
(Continued)

(58) Field of Classification Search

CPC ...... C12M 35/02; C12M 23/12; C12M 41/46; C12M 41/48; C12N 1/20; C12N 9/22;
(Continued)

(56) References Cited

U.S. PATENT DOCUMENTS

| | | | | |
|---|---|---|---|---|
| 6,387,671 B1 * | 5/2002 | Rubinsky | A61B 5/0536 | 435/173.7 |
| 2005/0282284 A1 * | 12/2005 | Rubinsky | A61N 1/327 | 435/459 |
| 2016/0122792 A1 * | 5/2016 | Peterson | C12P 19/34 | 435/91.2 |

OTHER PUBLICATIONS

Afridi, Muhammad Siddique, et al., "Harnessing microbial multitrophic interactions for rhizosphere microbiome engineering," Microbiological Research, Dec. 2022, 127199, 265.
(Continued)

*Primary Examiner* — Michael L Hobbs
(74) *Attorney, Agent, or Firm* — Carter, DeLuca & Farrell LLP; George Likourezos

(57) ABSTRACT

Examples of the present disclosure generally relate to systems, methods, and devices for performing electrochemical control and monitoring of bacterial gene expression to a precisely assigned level, and may be used, for example, for controlling the production of a protein of interest. In accordance with the present disclosure, a control system includes an apparatus configured to electrically induce gene expression; a detection system configured to detect level of the gene expression in the apparatus, the detection system configured to provide electrical signals indicative of the level of gene expression; and a computing device configured to implement closed loop control of the level of gene expression in the apparatus based on the electrical signals.

3 Claims, 19 Drawing Sheets

Specification includes a Sequence Listing.

(51) Int. Cl.

| | |
|---|---|
| ***C12M 1/34*** | (2006.01) |
| ***C12M 1/36*** | (2006.01) |
| ***C12N 1/20*** | (2006.01) |
| ***C12N 9/22*** | (2006.01) |
| ***C12N 13/00*** | (2006.01) |
| ***C12N 15/11*** | (2006.01) |

(52) U.S. Cl.
CPC ................ *C12N 1/20* (2013.01); *C12N 9/22* (2013.01); *C12N 13/00* (2013.01); *C12N 15/11* (2013.01); *C12N 2310/20* (2017.05); *C12N 2800/80* (2013.01)

(58) Field of Classification Search
CPC .... C12N 13/00; C12N 15/11; C12N 2310/20; C12N 2800/80
See application file for complete search history.

(56) References Cited

OTHER PUBLICATIONS

Atkinson, Joshua T., et al., "Real-time bioelectronic sensing of environmental contaminants," Nature, Nov. 2022, pp. 548-553, 611.7936.
Lindsay, Amber, and Brian MM Ahmer, "Effect of sdiA on biosensors of N-acylhomoserine lactones," Journal of bacteriology, Jul. 2005, pp. 5054-5058, 187.14.
Bikard, David, et al., "Programmable repression and activation of bacterial gene expression using an engineered CRISPR-Cas system," Nucleic acids research, Aug. 2013, pp. 7429-7437, 41.15.
Hanahan, Douglas, "Studies on transformation of *Escherichia coli* with plasmids," Journal of molecular biology, Jun. 1983, pp. 557-580, 166.4.
Dower, William J., Jeff F. Miller, and Charles W. Ragsdale, "High efficiency transformation of *E. coli* by high voltage electroporation," May 1988, pp. 6127-6145.
Cohen, Stanley N., Annie CY Chang, and Leslie Hsu, "Nonchromosomal antibiotic resistance in bacteria: genetic transformation of *Escherichia coli* by R-factor DNA," Proceedings of the National Academy of Sciences, Aug. 1972, pp. 2110-2114, 69.8.
Capecchi, Mario R., "High efficiency transformation by direct microinjection of DNA into cultured mammalian cells," Cell, Nov. 1980, pp. 479-488, 22.2.
Graham, Frank L., and Alex J. Van Der Eb, "A new technique for the assay of infectivity of human adenovirus 5 DNA," virology, Apr. 1973, pp. 456-467, 52.2.
Neumann, Eberhard, et al., "Gene transfer into mouse lyoma cells by electroporation in high electric fields," The EMBO journal, Jul. 1982, pp. 841-845, 1.7.
Tai-Kin Wong, Claude Nicolau, and Peter Hans Hofschneider, "Appearance of β-lactamase activity in animal cells upon liposome-mediated gene transfer," Gene, Jul. 1980, pp. 87-94, 10.2.
Gopal, T. Venkat, "Gene transfer method for transient gene expression, stable transformation, and cotransformation of suspension cell cultures," Molecular and Cellular Biology, May 1985, pp. 1188-1190, 5.5.
Yang, Ning-Sun, et al., "In vivo and in vitro gene transfer to mammalian somatic cells by particle bombardment," Proceedings of the National Academy of Sciences, Dec. 1990, pp. 9568-9572, 87.24.
Hitzeman, Ronald A., Louise Clarke, and John Carbon, "Isolation and characterization of the yeast 3- phosphoglycerokinase gene (PGK) by an immunological screening technique," Journal of Biological Chemistry, Dec. 1980, pp. 12073-12080, 255.24.
Luchansky, J. B., P. M. Muriana, and T. R. Klaenhammer, "Application of electroporation for transfer of plasmid DNA to lactobacillus, lactococcus, leuconostoc, listeria, pediococcus, bacillus, *staphylococcus*, enterococcus and propionibacterium," Molecular microbiology, Sep. 1988, pp. 637-646, 2.5.
Eagle, Harry, "Amino acid metabolism in mammalian cell cultures," Science, Aug. 1959, pp. 432-437, 130.3373.
Stanners, C. P., G. L. Eliceiri, and H. Green, "Two types of ribosome in mouse-hamster hybrid cells," Nature New Biology, Mar. 1971, pp. 52-54, 230.10.
Iscove, N. N., and F. Melchers, "Complete replacement of serum by albumin, transferrin, and soybean lipid in cultures of lipopolysaccharide-reactive B lymphocytes," The Journal of experimental medicine, Mar. 1978, pp. 923-933, 147.3.
Dulbecco, Renato, and G. Freeman, "Plaque production by the polyoma virus, " Virology 8.3 (1959): 396-397.
Li, Jinyang, et al., "Mediated electrochemistry to mimic biology's oxidative assembly of functional matrices," Advanced Functional Materials, Jul. 2020, 2001776, 30.30.
Tschirhart, Tanya, et al., "Electronic control of gene expression and cell behaviour in *Escherichia coli* through redox signalling," Nature communications, Jan. 2017, 14030, 8.1.
Bhokisham, Narendranath, et al., "A redox-based electrogenetic CRISPR system to connect with and control biological information networks," Nature communications, May 2020, 2427, 11.1.
Terrell, Jessica L., et al., "Bioelectronic control of a microbial community using surface-assembled electrogenetic cells to route signals," Nature Nanotechnology, Jun. 2021, pp. 688-697, 16.6.
Stephens, Kristina, et al., "Electronic signals are electrogenetically relayed to control cell growth and co-culture composition," Metabolic engineering communications, Dec. 2021, e00176, 13.
Kim, Eunkyoung, et al., "Redox is a global biodevice information processing modality," Proceedings of the IEEE, Apr. 2019, pp. 1402-1424, 107.7.
Vanarsdale, Eric, et al., "Redox electrochemistry to interrogate and control biomolecular communication," Iscience, Sep. 2020, 19 pages, 23.9.
Sultana, Sujala T., et al., "Electrochemical scaffold generates localized, low concentration of hydrogen peroxide that inhibits bacterial pathogens and biofilms," Scientific reports, Oct. 2015, pp. 1-10, 5.1.
Wang, Sally, Gregory F. Payne, and William E. Bentley, "Quorum sensing communication: molecularly connecting cells, their neighbors, and even devices," Annual review of chemical and biomolecular engineering, Jun. 2020, pp. 447-468, 11.
Wang, Sally, Gregory F. Payne, and William E. Bentley, "Quorum sensing componentry opens new lines of communication," The EMBO Journal, Sep. 2022, e112162, 41.18.
Surette, Michael G., Melissa B. Miller, and Bonnie L. Bassler, "Quorum sensing in *Escherichia coli*, *Salmonella typhimurium*, and Vibrio harveyi: a new family of genes responsible for autoinducer production," Proceedings of the National Academy of Sciences, Feb. 1999, pp. 1639-1644, 96.4.
Wang, Liang, et al., "Cyclic AMP (cAMP) and cAMP receptor protein influence both synthesis and uptake of extracellular autoinducer 2 in *Escherichia coli*," Journal of bacteriology, Mar. 2005, pp. 2066-2076, 187.6.
Quan, David N., et al., "Quorum sensing desynchronization leads to bimodality and patterned behaviors," PLoS computational biology, Apr. 2016, e1004781, 12.4.
Xavier, Karina B., and Bonnie L. Bassler, "Regulation of uptake and processing of the quorum-sensing autoinducer AI-2 in *Escherichia coli*," Journal of bacteriology, Jan. 2005, pp. 238-248, 187.1.
McCarty, Nicholas S., et al., "Multiplexed CRISPR technologies for gene editing and transcriptional regulation," Nature communications, Mar. 2020, 1281, 11.1.
Liao, Chunyu, et al., "Modular one-pot assembly of CRISPR arrays enables library generation and reveals factors influencing crRNA biogenesis," Nature communications, Jul. 2019, 2948, 10.1.
Barrangou, Rodolphe, et al., "CRISPR provides acquired resistance against viruses in prokaryotes," Science, Mar. 2007, pp. 1709-1712, 315.5819.
Deltcheva, Elitza, et al., "CRISPR RNA maturation by trans-encoded small RNA and host factor RNase III," Nature, Mar. 2011, pp. 602-607, 471.7340.
Chalfie, Martin, et al., "Green fluorescent protein as a marker for gene expression," Science, Feb. 1994, pp. 802-805, 263.5148.
March, J. C., G. Rao, and W. E. Bentley, "Biotechnological applications of green fluorescent protein," Applied microbiology and biotechnology, Sep. 2003, pp. 303-315, 62.

(56) References Cited

OTHER PUBLICATIONS

Kumar, S., P. Tiwari, and M. Zymbler, "Internet of Things is a revolutionary approach for future technology enhancement: a review," J Big Data 6, 2019, 21 pages, 111.
Motabar, Dana, et al., "Simple, rapidly electroassembled thiolated PEG-based sensor interfaces enable rapid interrogation of antibody titer and glycosylation," Biotechnology and Bioengineering, Jul. 2021, pp. 2744-2758, 118.7.
VanArsdale, Eric, et al., "Electrogenetic signal transmission and propagation in coculture to guide production of a small molecule, tyrosine," ACS synthetic biology, Feb. 2022, pp. 877-887, 11.2.
Li, Jinyang, et al., "Interactive materials for bidirectional redox-based communication," Advanced Materials, May 2021, 2007758, 33.18.
Wu, Gang, et al., "Metabolic burden: cornerstones in synthetic biology and metabolic engineering applications," Trends in biotechnology, Aug. 2016, pp. 652-664, 34.8.
Shang, Wu, et al., "Selective assembly and functionalization of miniaturized redox capacitor inside microdevices for microbial toxin and mammalian cell cytotoxicity analyses," Lab on a Chip, Aug. 2018, pp. 3578-3587, 18.23.
Shin, Minkyu, et al., "Nanomaterial-based biohybrid hydrogel in bioelectronics," Nano Convergence, Feb. 2023, 18 pages, 10.1,8.
Wang, Sally, Gregory F. Payne, and William E. Bentley, "Repurposing *E. coli* by engineering quorum sensing and redox genetic circuits," Gene Expression and Control. InTechOpen, 2018, Chapter 9, 22 pages.
VanArsdale, Eric, et al., "Electrogenetic signaling and information propagation for controlling microbial consortia via programmed lysis," Biotechnology and Bioengineering, May 2023, pp. 1366-1381, 120.5.
Milias-Argeitis, Andreas, et al., "Automated optogenetic feedback control for precise and robust regulation of gene expression and cell growth," Nature communications, Aug. 2016, 12546, 7.1.
Mansouri, Maysam, et al., "Smart-watch-programmed green-light-operated percutaneous control of therapeutic transgenes," Nature Communications, Jun. 2021, 3388, 12.1.
Gargalo, Carina L., et al., "Towards smart biomanufacturing: a perspective on recent developments in industrial measurement and monitoring technologies for bio-based production processes," Journal of Industrial Microbiology & Biotechnology: Official Journal of the Society for Industrial Microbiology and Biotechnology, Nov. 2020, pp. 947-964, 47.11.
Akyildiz, Ian F., et al., "The internet of bio-nano things," IEEE Communications Magazine, Mar. 2015, pp. 32-40, 53.3.
Krawczyk, Krzysztof, et al., "Electrogenetic cellular insulin release for real-time glycemic control in type 1 diabetic mice," Science, May 2020, pp. 993-1001, 368.6494.
Senturk, Seyda, Ibrahim Kok, and Fatmana Senturk, "Internet of nano, bio-nano, biodegradable and ingestible things: a survey," arXiv preprint, arXiv:2202, Feb. 2022, 12409.

* cited by examiner

FIG. 19A-E
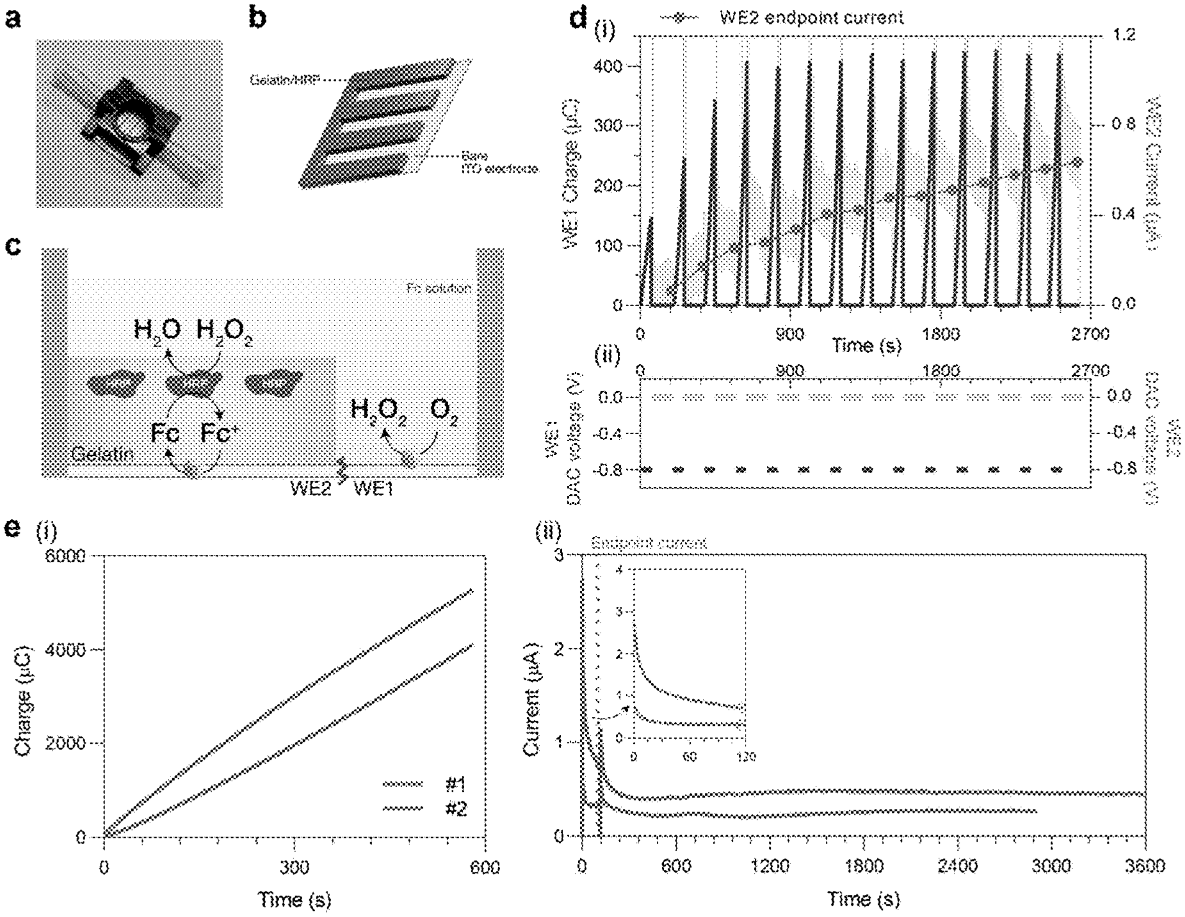

SEQUENCE LISTING

```
Sequence total quantity: 24
SEQ ID NO: 1            moltype = DNA  length = 144
FEATURE                 Location/Qualifiers
source                  1..144
                        mol_type = other DNA
                        organism = synthetic construct
SEQUENCE: 1
aaagttaaac aaaattattt gtagagggaa accgttgtgg tctccctgaa tatattatac  60
gagccttatg catgcccgta aagttatcca gcaaccactc atagacctag ggcagcagat  120
agggacgacg tggtgttagc tgtg                                         144

SEQ ID NO: 2            moltype = DNA  length = 918
FEATURE                 Location/Qualifiers
source                  1..918
                        mol_type = other DNA
```

```
                         organism = synthetic construct
SEQUENCE: 2
atgaatattc gtgatcttga gtacctggtg gcattggctg aacaccgcca ttttcggcgt  60
gcggcagatt cctgccacgt tagccagccg acgcttagcg ggcaaattcg taagctggaa  120
gatgagctgg gcgtgatgtt gctggagcgg accagccgta aagtgttgtt cacccaggcg  180
ggaatgctgc tggtggatca ggcgcgtacc gtgctgcgtg aggtgaaagt ccttaaagag  240
atggcaagcc agcagggcga gacgatgtcc ggaccgctgc acattggttt gattcccaca  300
gttggaccgt acctgctacc gcatattatc cctatgctgc accagacctt tccaaagctg  360
gaaatgtatc tgcatgaagc acagacccac cagttactgg cgcaactgga cagcggcaaa  420
ctcgattgcg tgatcctcgc gctggtgaaa gagagcgaag cattcattga agtgccgttg  480
tttgatgagc caatgttgct ggctatctat gaagatcacc cgtgggcgaa ccgcgaatgc  540
gtaccgatgg ccgatctggc aggggaaaaa ctgctgatgc tggaagatgg tcactgtttg  600
cgcgatcagg caatgggttt ctgttttgaa gccggggcgg atgaagatac acacttccgc  660
gcgaccagcc tggaaactct gcgcaacatg gtggcggcag gtagcgggat cactttactg  720
ccagcgctgg ctgtgccgcc ggagcgcaaa cgcgatgggg ttgtttatct gccgtgcatt  780
aagccggaac cacgccgcac tattggcctg gtttatcgtc ctggctcacc gctgcgcagc  840
cgctatgagc agctggcaga ggccatccgc gcaagaatgg atggccattt cgataaagtt  900
ttaaaacagg cggtttaa                                                918

SEQ ID NO: 3             moltype = DNA  length = 14
FEATURE                  Location/Qualifiers
source                   1..14
                         mol_type = other DNA
                         organism = synthetic construct
SEQUENCE: 3
tcacacagga aacc                                                    14

SEQ ID NO: 4             moltype = DNA  length = 95
FEATURE                  Location/Qualifiers
source                   1..95
                         mol_type = other DNA
                         organism = synthetic construct
SEQUENCE: 4
tatccatcct ccatcgccac gatagttcat ggcgataggt agaatagcaa tgaacgatta  60
tccctatcaa gcattctgac tgataattgc tcaca                             95

SEQ ID NO: 5             moltype = DNA  length = 30
FEATURE                  Location/Qualifiers
source                   1..30
                         mol_type = other DNA
                         organism = synthetic construct
SEQUENCE: 5
gcgtgttgtg gaagatccgg cctgcagcca                                   30

SEQ ID NO: 6             moltype = DNA  length = 76
FEATURE                  Location/Qualifiers
source                   1..76
                         mol_type = other DNA
                         organism = synthetic construct
SEQUENCE: 6
gttttagagc tagaaatagc aagttaaaat aaggctagtc cgttatcaac ttgaaaaagt  60
ggcaccgagt cggtgc                                                  76

SEQ ID NO: 7             moltype = DNA  length = 714
FEATURE                  Location/Qualifiers
source                   1..714
                         mol_type = other DNA
                         organism = synthetic construct
SEQUENCE: 7
atgagtaaag gagaagaact tttcactgga gttgtcccaa ttcttgttga attagatggt  60
gatgttaatg ggcacaaatt ttctgtcagt ggagagggtg aaggtgatgc aacatacgga  120
aaacttaccc ttaaatttat ttgcactact ggaaaactac ctgttccatg gccaacactt  180
gtcactactt tcgcgtatgg tcttcaatgc tttgcgagat acccagatca tatgaaacag  240
catgactttt tcaagagtgc catgcccgaa ggttatgtac aggaaagaac tatatttttc  300
aaagatgacg ggaactacaa gacacgtgct gaagtcaagt ttgaaggtga tacccttgtt  360
aatagaatcg agttaaaagg tattgatttt aaagaagatg gaaacattct tggacacaaa  420
ttggaataca actataactc acacaatgta tacatcatgg cagacaaaca aaagaatgga  480
atcaaagtta acttcaaaat tagacacaac attgaagatg gaagcgttca actagcagac  540
cattatcaac aaaatactcc aattggcgat ggccctgtcc ttttaccaga caaccattac  600
ctgtccacac aatctgccct ttcgaaagat cccaacgaaa agagagacca catgatcctt  660
cttgagtttg taacagctgc tgggattaca catggcatgg atgaactata caaa        714

SEQ ID NO: 8             moltype = DNA  length = 645
FEATURE                  Location/Qualifiers
source                   1..645
                         mol_type = other DNA
                         organism = synthetic construct
SEQUENCE: 8
atgatcgtac aaattggtcg gcgcgaagag ttcgataaaa aactgctggg cgagatgcac  60
```

```
aagttgcgtg ctcaagtgtt caaggagcgc aaaggctggg acgttagtgt catcgacgag  120
atggaaatcg atggttatga cgcactcagt ccttattaca tgttgatcca ggaagatact  180
cctgaagccc aggttttcgg ttgctggcga attctcgata ccactggccc ctacatgctg  240
aagaacacct tcccggagct tctgcacggc aaggaagcgc cttgctcgcc gcacatctgg  300
gaactcagcc gtttcgccat caactctgga cagaaaggct cgctgggctt ttccgactgt  360
acgctggagg cgatgcgcgc gctggcccgc tacagcctgc agaacgacat ccagacgctg  420
gtgacggtaa ccaccgtagg cgtggagaag atgatgatcc gtgccggcct ggacgtatcg  480
cgcttcggtc cgcacctgaa gatcggcatc gagcgcgcgg tggccttgcg catcgaactc  540
aatgccaaga cccagatcgc gctttacggg ggagtgctgg tggaacagcg actggcggtt  600
tcagcagcga acgacgaaaa ttacgccctt gcagcgtgat aataa                  645

SEQ ID NO: 9           moltype = DNA  length = 30
FEATURE                Location/Qualifiers
source                 1..30
                       mol_type = other DNA
                       organism = synthetic construct
SEQUENCE: 9
ggtatgatcg actgtgaagc tatctaacaa                                   30

SEQ ID NO: 10          moltype = DNA  length = 30
FEATURE                Location/Qualifiers
source                 1..30
                       mol_type = other DNA
                       organism = synthetic construct
SEQUENCE: 10
tgagaccagt ctcggaagct caaaggtctc                                   30

SEQ ID NO: 11          moltype = DNA  length = 219
FEATURE                Location/Qualifiers
source                 1..219
                       mol_type = other DNA
                       organism = synthetic construct
SEQUENCE: 11
ctcgaggttt tagagctatg ctgttttgaa tggtcccaaa acgcgtgttg tggaagatcc  60
ggcctgcagc cagttttaga gctatgctgt tttgaatggt cccaaaacgg tatgatcgac  120
tgtgaagcta tctaacaagt tttagagcta tgctgttttg aatggtccca aaacaaaaaa  180
aaaccccgcc cctgacaggg cggggttttt tttggatcc                         219

SEQ ID NO: 12          moltype = DNA  length = 167
FEATURE                Location/Qualifiers
source                 1..167
                       mol_type = other DNA
                       organism = synthetic construct
SEQUENCE: 12
aagcttttga cggctagctc agtcctaggt acagtgctag cggaaccatt caaaacagca  60
tagcaagtta aaataaggct agtccgttat caacttgaaa aagtggcacc gagtcggtgc  120
ttttttttcgc aaaaaacccc gcttcggcgg ggtttttttcg cgacgtc              167

SEQ ID NO: 13          moltype = DNA  length = 19
FEATURE                Location/Qualifiers
source                 1..19
                       mol_type = other DNA
                       organism = synthetic construct
SEQUENCE: 13
tgtttgacag cttatcatc                                               19

SEQ ID NO: 14          moltype = DNA  length = 34
FEATURE                Location/Qualifiers
source                 1..34
                       mol_type = other DNA
                       organism = synthetic construct
SEQUENCE: 14
gcgtccggcg tagagtcgtg tgagcaatta tcag                              34

SEQ ID NO: 15          moltype = DNA  length = 18
FEATURE                Location/Qualifiers
source                 1..18
                       mol_type = other DNA
                       organism = synthetic construct
SEQUENCE: 15
cacacgagcg tgttgtgg                                                18

SEQ ID NO: 16          moltype = DNA  length = 24
FEATURE                Location/Qualifiers
source                 1..24
                       mol_type = other DNA
                       organism = synthetic construct
SEQUENCE: 16
gtagagaaaa aagcaccgac tcgg                                         24
```

```
SEQ ID NO: 17          moltype = DNA  length = 38
FEATURE                Location/Qualifiers
source                 1..38
                       mol_type = other DNA
                       organism = synthetic construct
SEQUENCE: 17
gtcggtgctt ttttctctac ctctacgccg gacgcatc                        38

SEQ ID NO: 18          moltype = DNA  length = 43
FEATURE                Location/Qualifiers
source                 1..43
                       mol_type = other DNA
                       organism = synthetic construct
SEQUENCE: 18
ttccacaaca cgctcgtgtg tcgtgtgagc aattatcagt cag                  43

SEQ ID NO: 19          moltype = DNA  length = 34
FEATURE                Location/Qualifiers
source                 1..34
                       mol_type = other DNA
                       organism = synthetic construct
SEQUENCE: 19
ctaacggatc cgcttttttc tctacctcta cgcc                            34

SEQ ID NO: 20          moltype = DNA  length = 35
FEATURE                Location/Qualifiers
source                 1..35
                       mol_type = other DNA
                       organism = synthetic construct
SEQUENCE: 20
ctaagctcga gtgtgagcaa ttatcagtca gaatg                           35

SEQ ID NO: 21          moltype = DNA  length = 19
FEATURE                Location/Qualifiers
source                 1..19
                       mol_type = other DNA
                       organism = synthetic construct
SEQUENCE: 21
ggatcccatg gtacgcgtg                                             19

SEQ ID NO: 22          moltype = DNA  length = 29
FEATURE                Location/Qualifiers
source                 1..29
                       mol_type = other DNA
                       organism = synthetic construct
SEQUENCE: 22
ctagatttct cctctttaaa ggaattcgc                                  29

SEQ ID NO: 23          moltype = DNA  length = 41
FEATURE                Location/Qualifiers
source                 1..41
                       mol_type = other DNA
                       organism = synthetic construct
SEQUENCE: 23
tttaaagagg agaaatctag atgatcgtac aaattggtcg g                    41

SEQ ID NO: 24          moltype = DNA  length = 40
FEATURE                Location/Qualifiers
source                 1..40
                       mol_type = other DNA
                       organism = synthetic construct
SEQUENCE: 24
gcacgcgtac catgggatcc ttattatcac gctgcaaggg                      40
```

SYSTEMS, DEVICES, AND METHODS FOR CLOSED-LOOP BIOELECTRONIC CONTROL

CROSS-REFERENCE TO RELATED APPLICATIONS

This application claims the benefit of and priority to U.S. Provisional Application No. 63/363,004 filed on Apr. 14, 2022, which hereby is incorporated herein by reference in its entirety.

GOVERNMENT SUPPORT

This invention was made with government support under CBET1805274, ECCS1807604, and ECCS1926793 awarded by the National Science Foundation (NSF). The government has certain rights in the invention.

REFERENCE TO ELECTRONIC SEQUENCE LISTING

The application contains a Sequence Listing which has been submitted electronically in .XML format and is hereby incorporated by reference in its entirety. Said .XML copy, created on Jul. 2, 2026, is named "1475-103.xml" and is 25,195 bytes in size. The sequence listing contained in this .XML file is part of the specification and is hereby incorporated by reference herein in its entirety.

TECHNICAL FIELD

The present disclosure generally relates to systems, devices, and methods for performing electrochemical control and monitoring of bacterial gene expression to a precisely assigned level, and may be used, for example, for controlling the production of a protein of interest.

BACKGROUND

The concept of communication, or the transmission of information, builds the basis of the interconnected modern world we live in today. While current electronic devices are capable of freely exchanging information through electron transfer and electromagnetic waves, building smart systems that can connect both biological processes and electronic systems remains a challenging task due to their disparate communication modalities. Recently, redox-active molecules, due to their dual nature, were introduced as a novel medium to connect biological systems and electronics (1-4). No stranger to biology, redox-active molecules are present in the core of biological systems (e.g., NADH) serving as a bridge between electron transfer and molecular communication (5,6). When electrons flow between them, causing their distinct redox state to change, the redox molecules can also freely move in and out of the cell initiating a molecular dialogue. In addition, these redox activities can be easily and precisely controlled through routine electrochemical instrumentation, thus realizing programmed, automated regulation, which is believed to be one of the key functions in next generation biohybrid devices.

Employing peroxide ($H_2O_2$) as the electrochemical conduit, an electrogenetic system that enables information exchange between a living cell-embedded bioelectronics interface and an engineered microbial network was developed 3,4. Similarly, an electrically controlled, CRISPR-mediated toolkit for transcriptional regulation was built on the original "electrogenetics" archetype (1), adding an array of CRISPR functions to allow more genetically-focused intracellular control (2). Thus, the development of novel systems that can connect both biological processes and electronic systems is greatly needed.

SUMMARY

The present disclosure relates to a system for achieving, for example, real-time electrochemical control and monitoring of bacterial gene expression (the control and monitoring can occur while the gene expression is occurring) to a precisely assigned level, and for example controlling the production of a gene product of interest. The provided integrated system comprises four components: (i) a biological signal detection: gene-of-interest (GOI) expression level can be detected by using optical (fluorescence, luminescence) or electrochemical methods; (ii) a signal processing: converting biological signals into the digital signals which would be further processed by different algorithms for a particular output method (e.g., voltage, current, optical) to achieve feedback control of gene expression or remote control separate biological systems; (iii) a 3D-printed, ITO-based multi-chamber cell culture platform: This can be connected to the detection unit to receive the control signal from the signal processor, and generate the biological actuation signal i.e. $H_2O_2$; and (iv) an engineered bacteria: The engineered *E. coli* can be induced by the biological actuation signal generated from the device to express the GOI.

As a first component, a custom biological signal detection system is provided for precisely reading the fluorescence level of the cells under test, and in such a way that the raw optical signals are converted to electrical signals. FIG. 1 shows a diagram of such a detection system. The test probe can be moved between cell groups, the light source can be modulated for noise reduction, and the entire system can accommodate the custom cell culture device and its electrodes. The system is fully fiber-coupled in order to reduce noise and simplify alignment. The light source, detector, analog-to-digital converter and motorized stages are all controlled through a custom-made windows GUI as shown in FIG. 2. The cell activity can also be detected from the potentiostat circuit used in sections #2 and #3 if electrical rather than optical measurement is required.

As a second component, a signal processing unit is provided. The photomultiplier tube converts the incident fluorescence signal from the cells into a proportional voltage by means of an integrated transimpedance amplifier. This analog voltage is then digitized by a high resolution ADC. This is fed into a processor unit (currently a PC, but later will be a FPGA or other microprocessor). The processor then determines whether the level of the fluorescence signal is high enough to require production of H2O2 (or some other action). If so, the processor then enables its onboard potentiostat to control the cell culture device to produce it. The cells' response to this chemical production is then monitored by the fluorescence reader in #1, thereby enabling closed loop control. This processing unit is generalizable to any manner of input and output methods. FIG. 3 shows a block diagram of the signal processing unit.

As a third component, a 3D-printed, ITO-based multi-chamber cell culture platform is provided. Although conventional gold working electrodes offer great stability and electron delivery capability, the strong reflection could hinder the optic measurement and the detection of targeted fluorescent proteins expressed from the cell deposited on the electrode. To overcome this issue, we have developed an indium tin oxide (ITO)-based multi-chamber electrochemistry platform that aims for the high-throughput stimulation/measurement of a targeted microenvironment and cells using one-step 3D printing (FIG. 4). Using a 3D digital light processing (DLP) printing system, we have created device housing equipped with all detailed features; feature resolution is on the order of ~50 μm which offers finely tuned geometric parameters. There are 8 identical rectangular chambers for samples sitting by the center chamber for shared counter and reference electrodes that complete the circuit. The ITO working electrode sits at the bottom of the well which ensures contact to the samples and prevents bubbles that may change the surface area and further influence the input and output. Sharing the same reference and counter electrodes also provides extra stability that guarantees all chambers are running under the same standard. As an optoelectronic material, ITO glass provides a transparent optical window that enables a wider scope for various optical applications. Additionally, by coupling novel electrochemical fabrication, we can also evaluate important biological information via cyclic voltammetry or other electrochemical strategies by exploiting redox as a molecular communication modality. In turn, the devices can modulate the redox nature of the microenvironment, enabling new interpretations of biological responses.

As a fourth component, the present disclosure provides cells where the transcription of a gene-of-interest is regulated by electrochemical signaling and provides methods for real-time electrochemical control and monitoring of gene expression to a precisely assigned level, for example controlling the production of a gene product of interest. In an embodiment, the cells are recombinant cells into which expression vectors designed for expression of a gene-of-interest, or a reporter gene, under the transcriptional control of electrochemical signals have been introduced. Such cells include bacterial as well as eukaryotic cells. The introduced nucleic acid may be present independently of the genome of the host cell or in the state of being incorporated into the genome of the host cell.

In one aspect, an engineered bacteria harboring an eCRISPR system is provided. A peroxide-inducible electrochemical CRISPR (eCRISPR) system for controlling genetic expression was developed by rewiring *E. coli*'s native oxyRS regulon for combating oxidative stress from hydrogen peroxide. The guide RNA (gRNA) expression Is placed under the control of oxyS promoter and peroxide sensor, OxyR. To achieve CRISPR activation, the transcribed gRNA would form a complex with transcription factor ω subunit-fused deactivated Cas9 (dCas9ω) and activate the gene-of-interest (GOI; GFPmut2). Increasing levels of peroxide result in increased levels of green fluorescence, indicating that the expression of the GOI was activated. These peroxide-inducible CRISPRa bacteria were co-deposited with PEG-SH to form a film as described herein. After electrodeposition, 200 μL of LB and PBS mixture is added into the sample well, on top of the deposited film. Voltage (−0.8 V) is then applied to the films for various times from 5-30 minutes. After 4 hours of incubation at 37° C., the device is placed under a confocal microscope for a parallel observation. With increasing charge applied, both the percentage of *E. coli* expressing GFPmut2 and the intensity of green fluorescence had gone up, which agreed with observations with suspension culture. The increasing fluorescence may also be measured through the electronic device disclosed herein and the output signal can be further processed by a signal processing unit's algorithms to control the potentiostat for voltage output. This will in turn influence the production of peroxide and change the GOI's expression level, thus completing the bio-electronic control loop.

Another aspect of the present disclosure pertains to nucleic acids encoding the gene-of-interest, or a reporter gene, wherein expression of said gene-of-interest or reporter gene is mediated by electrochemical signaling. Nucleic acids may also include those encoding for Cas9 protein (inhibitor (CRISPRi) or activator (CRISPRa)) and a gRNA of interest. Such nucleic acids may be introduced into a variety of different expression vectors, including for example, bacterial, and eukaryotic expression vectors for expression of the gene-of-interest, or reporter gene.

In still another aspect, a method is provided of preparing a gene product of interest in a cell wherein expression of the gene product of interest is under the control of electrochemical signaling. The preparation method comprises (i) culturing the cells as described herein having expression of a gene-of-interest mediated by electrochemical signaling; (ii) providing an electrochemical signal; and (iii) allowing for expression of the gene product of interest. In a further step, the gene product of interest is purified from the cell culture.

BRIEF DESCRIPTION OF THE FIGURES

(FIG. 4A) Top view of the device. The 3D printed housing is photocured with a precut square ITO glass to form the final device. (FIG. 4B) Bottom view of the device. The transparency of ITO glass enables optical monitoring while performing redox applications. (FIG. 4C) The casted salt bridge works as the electron delivery pathway between the working electrodes at the bottom of the sample chambers and the center counter electrode. (FIG. 4D) The miniature device can run 8 samples simultaneously with a very small sample volume. (FIG. 4E) The manufacturing step for the device.

(FIG. 5A) Electrogenetics allows direct electron flow to alter gene expression and generate digitizable optical signals for establishing connectivity with electronic systems. Information can thus be propagated within the network to other workstations and users through wireless connection enabled by the internet. The connected bio-electrochemical setup at a separate location demonstrates electronic-chemical-electronic signal conversion, through encoding electronic input into a chemical signal (peroxide) followed by biochemically decoding the chemical signal back to an electronic output. (FIG. 5B) Transformation in signaling modality enables connection of biology to electronics. An encoded electronic input is first transduced to a chemical signal interpretable by biological systems to generate two different biological outputs. On top illustrates the optical signal, serving as the conduit to electronic systems after digitization. The bottom depicts QS signaling molecules that provide information to other biological systems.

(FIG. 6A) ITO-based, 3D-printed biohybrid device. The clear ITO glass serves as the working electrode and allows for optical observations. An Ag/AgCl electrode is used as the reference electrode, and a Pt wire (right, mounted on connector) is the counter electrode. The three electrodes are connected through the salt bridge (1 M KCl in 1% agarose) casted in the central well of the device. (FIG. 6B) Schematic illustration of *E. coli* and PEG-SH co-deposition. An oxidizing voltage (0.8 V) is used to oxidize the thiol group in PEG-SH and initiate gelation. (FIG. 6C) Z-stack image of the "artificial biofilm" containing engineered *E. coli* that constitutively express GFP (DH5α-sfGFP). (FIG. 6D) Thickness of the deposited "artificial biofilm" as estimated through confocal Z-stack images. Film thickness is customizable by varying deposition time. Circle symbols represent separate replicates (n=4). Error bars represent the standard deviation. (FIG. 6E) $H_2O_2$ generated in the ITO-based electrochemical platform as correlated to applied charge. Error bars represent the standard deviation (n=4).

(FIG. 7B) General workflow and setup for experiments on an 'artificial biofilm'. (FIG. 7C) Confocal images of *E. coli* harboring the eCRISPRa-GFP genetic cassette that were embedded in the PEG-SH film. Varying times of electrical induction and the resulting charges (millicoulomb; mC) applied to the cells are indicated below. 200 μM of $H_2O_2$ was exogenously added to culture media to activate the oxyS promoter as the positive control. Top: brightfield; Middle: Merged; Bottom: FITC filter. (FIG. 7D) Percentage of *E. coli* in the PEG-SH film that were activated through eCRISPRa. (FIG. 7E) AI-1 assay indicating the amounts of AI-1 generated via CRISPRa. (FIG. 7F) Measured fluorescence in coculture comprised of eCRISPRa lasI cells and AI-1 fluorescent reporters (NEB10β+LasR_S129T-GFPmut3). eCRISPRa last cells were confined in an 'artificial biofilm' submerging in planktonic culture of AI-1 fluorescent reporters. For all figures, the height of the bar represents the mean, and error bars represent the standard deviation (n≥2). Individual replicates were indicated as open circles.

(FIG. 8A) Schematic of luxS eCRISPRi to inhibit AI-2 QS signaling. luxS specific gRNA LuxS1 is expressed under oxyS promoter in pSC-LuxS1. Both pSC-LuxS1 and pdCas9ω were transformed into NB101 allowing gRNA expression. (FIG. 8B) Measured AI-2 activity of the CM samples collected at various times post-induction. In-film eCRISPRi cells were electro-induced for 0 or 30 minutes 3 h after deposition. (FIG. 8C) Schematic of multiplexed eCRISPR for engineering a 'bilingual' strain. gRNAs sg108 and LuxS1 were flanked with the DR sequence and placed downstream of the oxyS promoter in pSC-sg108+LuxS1. tracrRNA was individually expressed under a synthetic constitutive promoter. Both pSC-LuxS1 and pdCas9ω were transformed into NB101 allowing gRNA expression. Plasmids pSC-sg108+Lux1, pdCas9ω, and pMC-lasI-LAA were all transformed into NB101 allowing multiplexed gRNA expression. (FIG. 8D) Measured AI-1 levels and AI-2 activity of the CM samples collected 7 h post-deposition. In-film 'bilingual' cells were electro-induced for 0 or 30 minutes at 0 or 0 and 3 h post-deposition. For all figures, the height of the bar represents the mean, and the error bars represent the standard deviation (n≥3). Individual replicates are indicated as open circles.

(FIG. 9B) Automation experiment workflow. Artificial biofilm containing engineered bacteria are assembled onto the ITO electrode of the biohybrid device. Its level of gene expression, represented by the emitted fluorescence, is constantly monitored by the Biospark system and sent to the PC (diamond) for processing. The custom algorithm (FIG. 17) then determines the status of expression via calculating the ratio of the slopes. When the user-customizable ratio threshold is met, the potentiostat is triggered to apply an induction voltage for a set time or charge. The experiment is automatically terminated when the fluorescence level is over the user-set induction level threshold. (FIG. 9C) Autonomous dynamic control of eCRISPRa-regulated gene expression. Top: fluorescence level of the artificial biofilm containing the engineered eCRISPRa bacteria (NB101 harboring pSC-O108, pdCas9ω, and pMC-GFP). Fluorescence measurement was taken every 15 minutes (0.25 h). Experiment ended automatically when fluorescence is over the induction level threshold. The fluorescence level of the negative control to which no induction voltage is applied is shown. Vertical zones indicate the periods when the induction voltage (−0.8 V) is applied. A total charge of 2 mC was applied to the cells in each zone. Bottom: Ratio to $S_{max}$ computed by the custom algorithm. Ratio threshold was set at 0.4. The first vertical line indicates when the algorithm applied the initial induction voltage. Additional vertical lines indicate when two consecutive ratios were below set threshold, thus meeting the ratio threshold and triggering the potentiostat to apply induction voltage. The dotted vertical line indicates when both the ratio threshold and the induction level threshold were met, hence no voltage was applied, and the experiment was terminated. Open circle, open square, and filled circle represent the mean and error bars represent the standard deviation of individual replicates (n=2).

(FIG. 10A) System diagram of the complete Bio-Nano Things network. (FIG. 10B) Automated feedback control of eCRISPRa-regulated gene expression. Local (i): fluorescence level of the artificial biofilm containing the engineered eCRISPRa bacteria (NB101 harboring pSC-O108, pdCas9ω, and pMC-GFP). Fluorescence measurement was taken every 15 minutes (0.25 h). Open squares and line indicate the mean in fluorescence level of the negative control to which no induction voltage was applied. Vertical zones indicate the periods when the induction voltage (−0.8 V) is applied. A total charge of 2 mC was applied to the cells in each zone. The termination zone indicates when the selected sample was being photobleached. Local (ii): Ratio to $S_{max}$ computed by our custom algorithm. Ratio threshold was set at 0.4. The first vertical line indicates when the algorithm applied the initial induction voltage. Additional vertical lines indicate when two consecutive ratios were below set threshold, thus meeting the ratio threshold and proceeded to trigger the remote 'actuation checkpoint'. Remote: Current threshold (dotted line) was set at 1.1 μA. The last vertical line indicates when the current threshold was met, which prompted the PC at the remote location to send a text message to users. Error bars represent the standard deviation of individual replicates (n=2).

(FIG. 11B) Spatially deposited engineered *E. coli*. *E. coli* (NB101 with plasmids pSC-O108, pdCas9ω, and pMC-lasILAA) were grown to mid-log phase and harvested via centrifugation. A portion of the harvested bacteria were exposed to heat in order to generate dead *E. coli*. Both live and dead cultures were stained with a bacterial viability kit then were added into PEG-SH solution for electrodeposition. Top: Image of PEG-SH hydrogel containing stained live *E. coli* cultures. (Green fluorescence filter). Bottom: Image of PEG-SH hydrogen containing stained dead *E. coli* cultures. (Red fluorescence filter).

(FIG. 12A) Fluorescence of NB101 harboring pSC-O108, pdCas9ω), and pMC-GFP. 2 hours (light bar) and 4 hours (dark bar) after $H_2O_2$ induction. Error bars represent the standard deviation. Open circles represent individual replicates (n=5). (FIG. 12B) Relative fold change of gRNA (sg108) expression induced with various levels of $H_2O_2$. Error bars represent the standard deviation (n=3). Open circles represent individual replicates.

(FIG. 13B) AI-1 bioassay standard curve. Error bars represent the standard deviation (n=3). The calibration curve was generated via linear interpolation of experimental data, and the dash lines represent the 95% confidence interval. (FIG. 13C) Fluorescence response from AI-1 inducible strain (NEB10β+LasR_S129T-GFPmut3). Error bars represent the standard deviation (n=3).

(FIG. 14A) Extracellular AI-2 activity of NB101 cells constitutively expressing either a control gRNA (dark bar) or luxS-specific gRNA LuxS1 (lighter bar) at various time points after reinoculation. No glucose was added to LB media for inhibiting AI-2 uptake. (FIG. 14B) Extracellular AI-2 activity of NB101 cells carrying plasmids pSC-LuxS1 and pdCas9ω induced with 0 or 200 μM of peroxide at $OD_{600}$=0.4. CM samples were collected at various time points after re-inoculation. A final concentration of 0.8% (w/v) glucose was added to LB media for inhibiting AI-2 uptake. (FIG. 14C) Extracellular AI-2 activity profile of NB101 cells harboring no plasmid (grey) or eCRISPRi components (pSC-LuxS1 and pdCas9ω) when assembled as "artificial biofilms". (FIG. 14D) Measured AI-1 concentration (i) or AI-2 activity (ii) secreted from 'bilingual' cells 7 h post-reinoculation. Labels on the x-axis indicate when the cells received 200 μM $H_2O_2$ for inducing expression of both gRNAs. For all figures, bar height represents the mean and error bars represent the standard deviation (for (a)-(c) n=3, for (d) n=2). Open circle represents the individual replicates.

(FIG. 16A) Green fluorescence particles were co-deposited with PEG-SH to various concentrations for simulating fluorescence emitted from engineered bacteria in the 'artificial biofilm'. The resulting hydrogel was submerged in 150 μL of 20% LB, which is identical to the cell experiments. Fluorescence was read using Biospark and the Tecan Spark® microplate reader. (FIG. 16B) Relative measured fluorescence from fluorescence particles/PEG-SH hydrogel. The four samples were read in the sequence of 0%→0.1%→0.25%→1% consecutively for 8 cycles.

(FIG. 17A) "Growth curve" of engineered *E. coli* entrapped in artificial biofilm from measured fluorescence of DH5α-sfGFP cells co-deposited with PEG-SH. A "lag-phase" of approximately 1.25 hours was observed in which there was no increase in fluorescence detected, suggesting that there was no growth during this period. Open circles represent the mean fluorescence, and the dashed curves represent the error from individual replicates (n=4). (FIG. 17B) Selected representation of the gene expression dynamic of in-film peroxide reporters (NEB10β+pOxy-sfGFP). Vertical zone indicates when voltage was applied for electroinduction. The uninduced negative control is plotted. Open circles and squares represent the mean and error bars represent the standard deviation of individual replicates (n=2). (FIG. 17C) Fold changes in fluorescence before and after electroinduction. Bar height represents the mean and error bars represent the standard deviation (n=2). Individual replicates are indicated by the open circles. (FIG. 17D) Custom algorithm to monitor gene expression. Since the fluorescence was taken at a fixed time interval, we defined the slope as the difference between two neighboring fluorescence measurements. The algorithm will store and update the value of the maximum slope. It will also compute the ratio between the current slope and the maximum slope ($S_{max}$). If two consecutive ratios fall below the user-set ratio limit, the algorithm considers the ratio threshold met and will initiate electro-induction via the potentiostat. The $S_{max}$ will in turn return to 0 and start a new cycle.

FIG. 19A-E. Bio-electrochemical platform serving as an actuation checkpoint in the smart feedback-control system (FIG. 19A) Custom electrochemical platform with a patterned ITO glass slide attached to a 3D-printed housing. (FIG. 19B) A patterned electrode is generated via laser-cutting the ITO-coated glass into a zig-zag pattern to ensure the generated $H_2O_2$ is in the vicinity of the HRP/gelatin hydrogel for detection. (FIG. 19C) Working mechanism of the electrochemical "actuation checkpoint" platform. A gelatin hydrogel containing horseradish peroxidase (HRP) is deposited initially on working electrode 2 (WE2). Working electrode 1 (WE1), which consists of just the bare ITO electrode, is tasked to generate $H_2O_2$ when we apply a reducing voltage. HRP in the gelatin gel on WE2 then catalyzes the generated $H_2O_2$, and the resulting electron cycles with the electrochemical mediator ferrocene that is present in the solution. A current (from the cycling of ferrocene) can be read when an oxidizing voltage is applied (0 V vs Ag/AgCl). (FIG. 19D) Demonstration of data writing and storage. Generated charge on WE1 and current obtained from WE2 were plotted over the time. (FIG. 19E) Demonstration of "long-term" data storage. Total charge from applying −0.8 V on WE1 for 600 s is plotted in (i). The following currents obtained for up to an hour on WE2 are plotted in (ii) (inset: 0-120s). Red line and open circle indicate when the endpoint current was recorded (at 120 s).

DETAILED DESCRIPTION

The present disclosure provides systems and methods for controlling and monitoring electrically induced gene expression. As will be described by an example below, electric voltage may be applied to generate peroxide for a peroxide-mediated, electrically inducible CRISPR transcriptional activation (CRISPRa) system, which may be monitored by using plasmid pMC-GFP in which the expression of reporter gene gfpmut2 is upregulated by the CRISPR components. In such an example, the resultant fluorescence would be indicative of the gene-of-interest ("GOI") expression level. Increasing levels of peroxide result in increased levels of green fluorescence, indicating that the expression of the GOI was activated. The fluorescence may be detected by a transducer which converts optical signals to electrical signals to indicate the GOI expression level. The electrical signals may be processed by a computing system to implement closed-loop control of the applied electric voltage to regulate the peroxide generation and, thereby, regulate the GOI expression level. While the present disclosure primarily describes this example, the example is merely illustrative of an electrically controllable gene expression system. It is intended that other electrically controllable gene expression systems and methods would be within the scope of the present disclosure.

The present disclosure provides an example of a system for achieving real-time electrochemical control and monitoring of bacterial gene expression to a precisely assigned level, for example controlling the production of a gene product of interest. The provided example of an integrated system includes four components:

(i) A biological signal detection: gene-of-interest (GOI) expression level can be detected by using optical (fluorescence, luminescence) or electrochemical methods.

(ii) a signal processing: converting biological signals into the digital signals which would be further processed by different algorithms for a particular output method (e.g., voltage, current, optical) to achieve feedback control of gene expression or remote control separate biological systems.

(iii) a 3D-printed, ITO-based multi-chamber cell culture platform: This can be connected to the detection unit to receive the control signal from the signal processor, and generate the biological actuation signal i.e. $H_2O_2$; and (iv) an engineered bacteria: The engineered *E. coli* can be induced by the biological actuation signal generated from the device to express the GOI. These components are described in more detail below in connection with the drawings.

Figure 1:
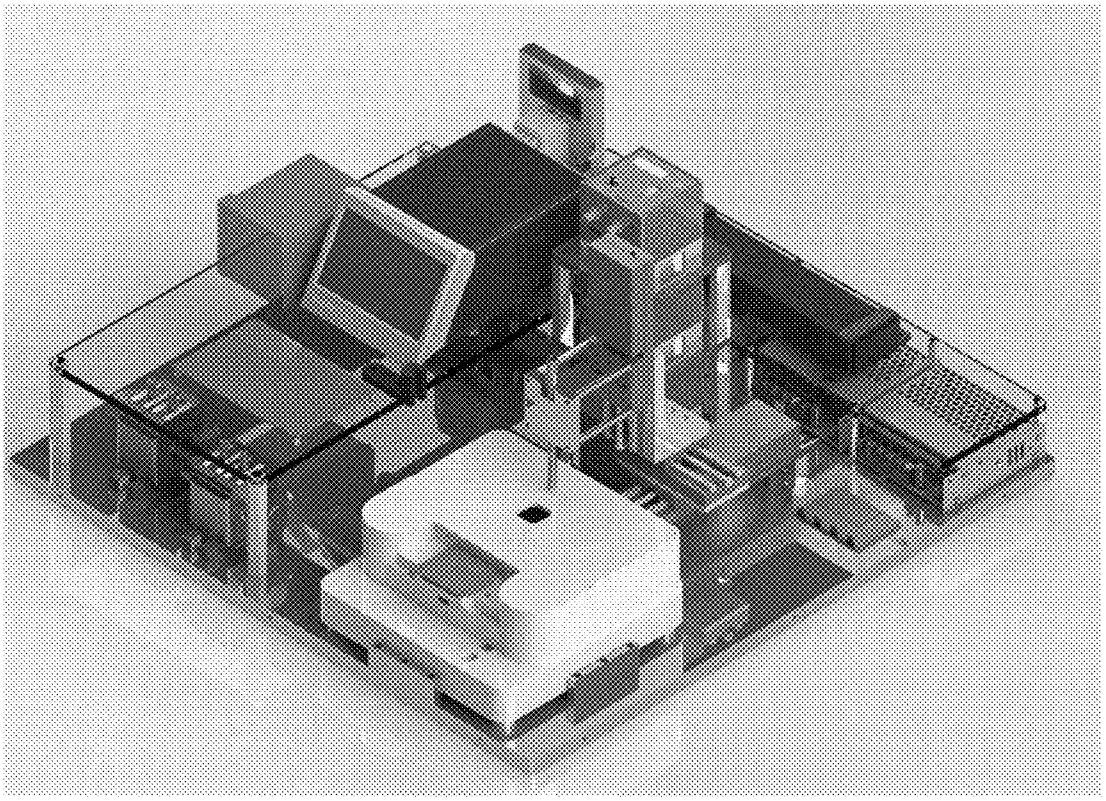
FIG. 1 is a diagram of an example detection system.

Referring now to FIG. 1, there is shown an example of a detection system for detecting fluorescence level and for converting the raw optical signals to electrical signals. The prototype system includes a fiber probe, an optional detector filter, a photomultiplier tube (PMT), and an analog-to-digital converter (ADC)). A test bed includes biological samples which fluoresce when a gene-of-interest (GOI) is expressed. The fluorescence is picked up by the fiber probe and guided to the optional detector filter, which operates to filter out optical noise, such as low-level ambient light. In situations where optical noise is not a concern, the detector filter may be omitted.

The output of the detector filter is coupled to the photomultiplier tube. The photomultiplier tube converts the fluorescence signal from the biological sample into a proportional voltage using, e.g., an integrated transimpedance amplifier. This analog voltage is then digitized by the ADC, which may be a high-resolution ADC, to provide an electrical signal indicative of the GOI expression level. In embodiments, the detection system is fiber-coupled to reduce noise and simplify alignment. In embodiments, the digital samples provided by the ADC may be communicated to and stored in an electronic storage device (not shown), which may be local to the detection system or remote from the detection system. Altogether, the fiber probe, the optional detector filter, the photomultiplier, and the ADC, may be referred to as a measurement sensor, and the outputs of the ADC may be referred to as sensor measurements.

In FIG. 1, the test bed may include multiple sample wells. To measure the GOI expression level of each well, the detection system may include one or more motors coupled to the fiber probe that move the fiber probe to the sample well to be measured. The scanning motor is merely an example and in embodiments, multiple fiber probes may be deployed. A particular embodiment is described as follows.

Fluorescence Measurement Module

The fluorescence reader may include a 470 nm excitation light source and driver (Thorlabs #M470F4 and #DC2200) that sends light to a fiber-coupled filter mount (Thorlabs #FOFMS) via a 1000 μm diameter core multimode fiber (Thorlabs #FT1000EMT-CUSTOM). An OD6 fluorescence filter (Edmund Optics #67-027) can be used to set the excitation band. This light is then directed onto the test target via a fiber coupled reflection probe (Thorlabs #RP22). The emission from the target is collected by the other fibers in this bundle and directed to a second fiber coupled filter mount (Thorlabs #FOFMS) which contained two OD6 emission filters (Edmund Optics #67-030). The filtered light in turn passed through another fiber (Thorlabs #FT1000EMT-CUSTOM) to a fluorescence enhanced PMT (Thorlabs

#PMT2101) where it can be converted to an electrical signal that travels to the Analogue to Digital Converter (ADC) on a FPGA potentiostat board. A 3-axis motion platform having three stepper motor kits (Thorlabs #KMTS50E) connected together with a base plate (Thorlabs #MTS50A-Z8), XY plate (Thorlabs #MTS50B-Z8) and right-angle plate (Thorlabs #MTS50C-Z8) can be used to allow x, y, and z-axis movement of the probe.

The system illustrated and described in connection with FIG. 1 is merely an example, and variations are contemplated to be within the scope of the present disclosure.

Figure 2:
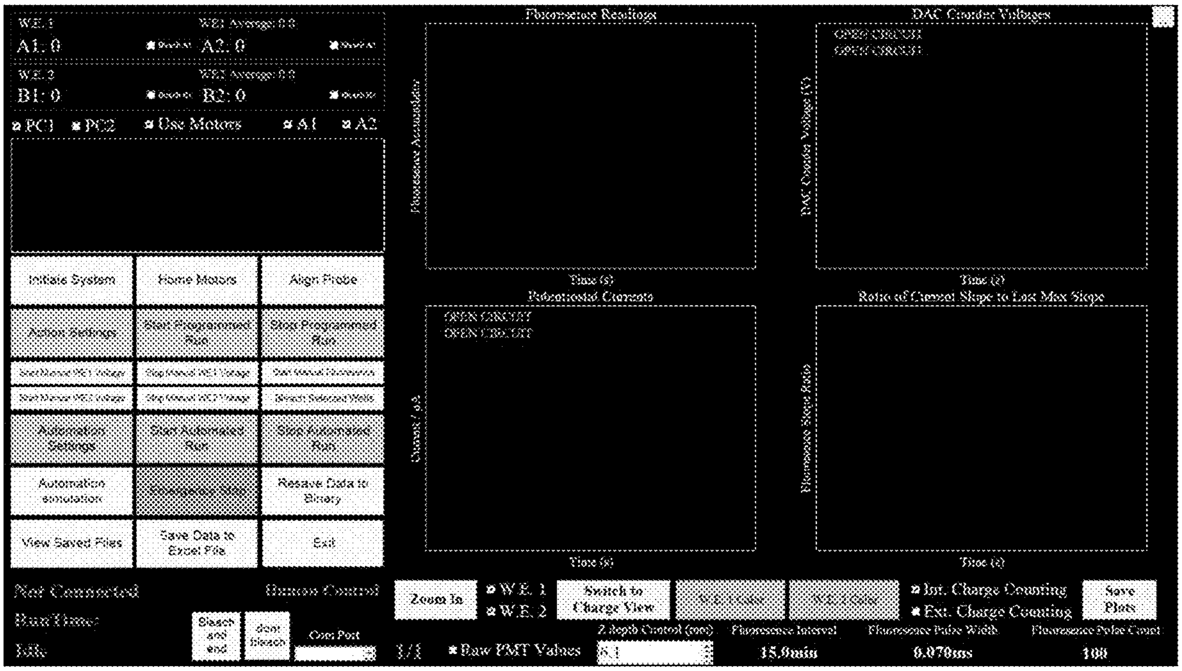
FIG. 2 is a diagram of an example graphical user interface.

FIG. 2. shows a graphical user interface (GUI) which can control the detection system of FIG. 1. The light source, detector, analog-to-digital converter, and motor(s) can be controlled through the GUI, and various data may be displayed in the GUI. The data may be retrieved from an electronic storage system, such as that described in connection with FIG. 1. The GUI is merely an example, and variations are contemplated to be within the scope of the present disclosure.

Figure 3:
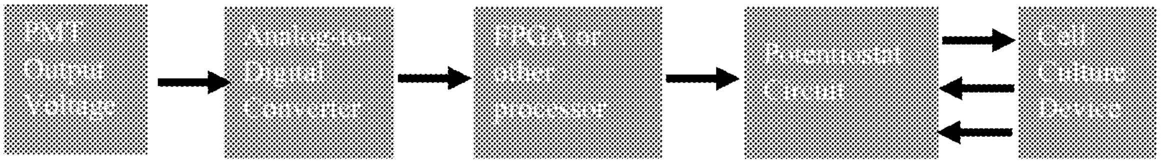
FIG. 3 is a block diagram of an example signal processing flow.

FIG. 3 is a block diagram of a closed loop control system for controlling the gene expression of a GOI. The block diagram includes a PMT, an ADC, a field-programmable gate array (FPGA) or other processor, a potentiostat circuit, and a cell culture device. The PMT and ADC were described above. The digital samples provided by the ADC may be referred to as sensor measurements, as described above. The FPGA or other processor is configured to analyze the sensor measurements to control the GOI expression level. For example, the FPGA or processor can determine whether the level of the fluorescence signal indicates that production of $H_2O_2$ (or some other action) should be maintained, increased, or decreased. Based on the determination, the processor controls the potentiostat to apply a corresponding voltage to maintain, increase, or decrease the $H_2O_2$ production level in the cell culture device. The resulting fluorescence is measured by the PMT, thereby enabling closed loop control. In embodiments, the potentiostat may be a two-channel arbitrary waveform potentiostat with simultaneous sampling of up to two PMT sensors.

A FPGA-potentiostat implementation is described as follows.

FPGA-Potentiostat

A potentiostat through fabrication and assembly of a FPGA board is described. The core component is a Spartan-7 module (Opal Kelly #XEM7305) and breakout board (Opal Kelly #BRK7305). Power can be supplied via an ultralow-noise linear power supply (Acopian #DBS-50). While many components can be used on the potentiostat board, the three primary components of interest included (a) a femtoampere input bias current op-amps (Analog Devices #ADA4530), (b) a 16-bit multichannel Digital-to-analog converter (DAC) (Analog Devices #AD5765), and a 18-bit multichannel ADC (Texas Instruments #ADS8698).

Referring again to FIG. 2, aspects of the process of FIG. 3 may be controlled by a GUI program. Functions may include adjusting metrics related to the (a) various potentiostat mode (e.g., chronoamperometry mode, cyclic voltammetry mode, manual, AI controlled), (b) potentiostat settings (e.g., voltage, pulse period, slew rate, max charge, etc.), (c) fluorescence reading (e.g., pulse width, pulse count, measurement interval), and (d) AI control (e.g., AI mode, ratio thresholds, expression level target, SMS settings, etc. . . . ), among others. Data may be saved in a binary format and could be exported into an Excel spreadsheet (.xlsx) or into other formats. Various data may be shown in the GUI (e.g., FIG. 2), such as four real-time diagrams on the main screen of the program displayed the fluorescence values, potentiostat currents and charges, applied counter voltages, and the CV curve or fluorescence slope ratios.

FIG. 3 is merely an example of a control system. The blocks of FIG. 3 may be generalizable to any manner of input and output methods for controlling gene expression levels. For example, in embodiments, the gene expression level may be measured using electrochemical sensors rather than an optical sensor. For example, cell activity may be detected by the potentiostat circuit when electrical (rather than optical) measurement is applicable. In embodiments, the gene expression level may be controlled by a device other than a potentiostat circuit. The processor may be any computing device, such as, without limitation, a digital signal processor, a microcontroller, a microprocessor, and/or an application specific integrated device (ASIC), among other computing devices.

Figure 4:
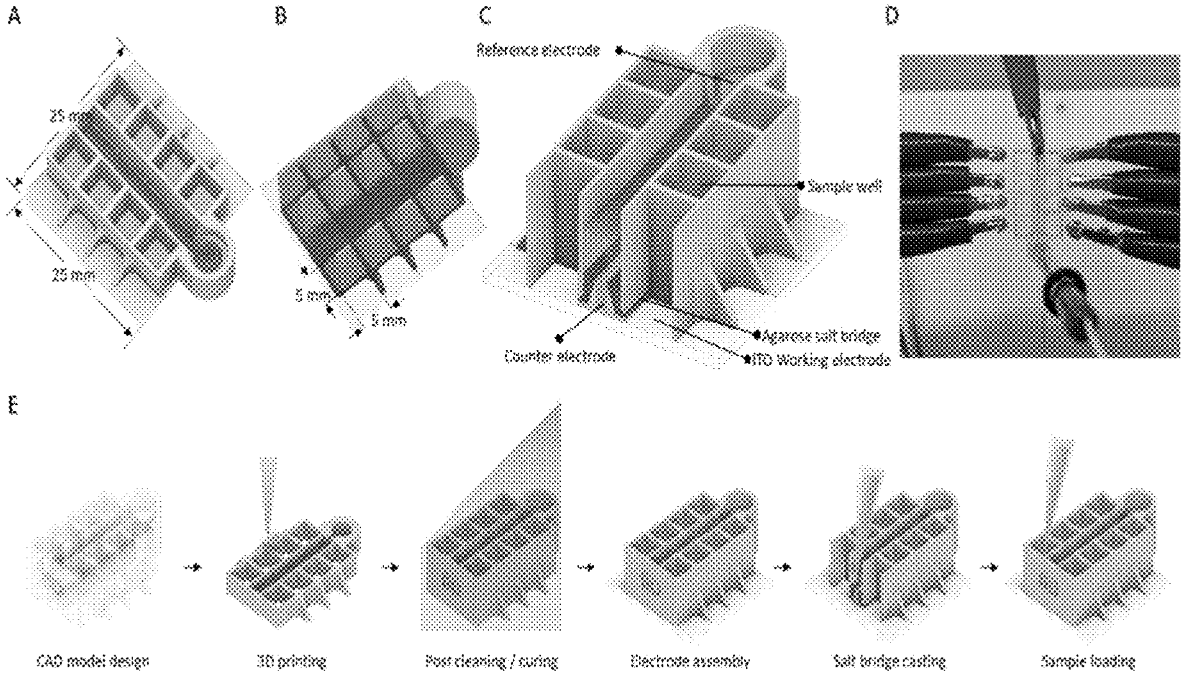
FIG. 4A-E are diagrams of an example apparatus for performing gene expression, including, for example, a 3D printed ITO-based multi-chamber electrochemistry platform.

FIG. 4 shows an example of an apparatus for performing gene expression, including, for example, a cell culture device that may be controlled by the process of FIG. 3. The device may include electrodes of a potentiostat and/or may include the potentiostat. In embodiments, although conventional gold working electrodes offer stability and electron delivery capability, the strong reflection could hinder the optic measurement and the detection of targeted fluorescent proteins expressed from the cell deposited on the electrode. In embodiments, an indium tin oxide (ITO)-based multi-chamber electrochemistry platform can be used to provide a high-throughput stimulation/measurement microenvironment. In embodiments, the device may be produced using 3D printing, such as produced using a 3D digital light processing (DLP) printing system, which has feature resolution on the order of ~50 μm and offers finely tuned geometric parameters. An example is illustrated in FIG. 4.

In the example of FIG. 4, there are eight identical rectangular chambers for samples positioned by a center chamber for shared counter and reference electrodes that complete the circuit. Separate ITO working electrodes sit at the bottom of the wells, which ensures contact to the samples and prevents bubbles that may change the surface area and further influence the input and output. Sharing the same reference and counter electrodes also provides extra stability that guarantees all chambers are running under the same standard. As an optoelectronic material, ITO glass provides a transparent optical window that enables a wider scope for various optical applications. Additionally, by coupling electrochemical fabrication, important biological information, via cyclic voltammetry or other electrochemical strategies by exploiting redox as a molecular communication modality, may be evaluated. In turn, the devices can modulate the redox nature of the microenvironment, enabling new interpretations of biological responses.

Regarding the example 3D printed ITO-based multi-chamber electrochemistry platform, FIG. 4 shows: (A) a top view of the device, where the 3D printed housing is photo-cured with a precut square ITO glass to form the final device; (B) a bottom view of the device, where the transparency of ITO glass enables optical monitoring while performing redox applications; (C) a casted salt bridge, which works as the electron delivery pathway between the working electrodes at the bottom of the sample chambers and the center counter electrode; (D) a miniature device which can run eight samples simultaneously with a very small sample volume; and € a manufacturing process for the device, which uses a CAD model and uses DLP 3D printer to fabricate the housing followed by post cleaning and UV curing process. The housing is then attached to an ITO electrode with same photosensitive resin cured by UV. The salt bridge is then casted using agarose gel and 1M KCl solution.

Fabrication of the Biohybrid Electronic Device

The custom-designed housing was printed with a 3D printer and was then attached to the ITO-coated glass slide (Sigma) as the working electrode using the same resin and UV-curing (company). The Ag/AgCl reference electrode (Pine Research) can be inserted from the side well into the central well containing the salt bridge. Agarose salt bridge, consisting of 0.1% agarose in 1M KCl, was heated and added into the central well. After the agarose solidified, 1M KCl was added to submerge the salt bridge. A separate custom connector was also printed (with a 3D printer), and a Pt wire was attached as the counter electrode. With the device fully assembled, the counter electrode was immersed in the 1M KCl solution present in the central salt bridge well.

Electrode Chip Fabrication

Gold patterned electrodes from Platypus Technologies and Pine Research may be used. Steps for fabricating the custom patterned gold electrode on silicon wafers may be as follows: First, metal deposition was performed on standard 4-inch silicon wafers using a Denton thermal evaporator (Denton Vacuum), with metal deposition rates of 2-3 Å s-1. Specifically, a 50 nm chromium adhesion layer was evaporated, followed by 100 nm gold. Next, photolithography utilized direct writing of photoresist via a DWL66fs laser writer (Heidelberg Instruments), guided by a laser exposure map designed in AutoCAD (Autodesk). Photoresist spin-coating and development steps were performed using an EVG120 automated resist processing system (EV Group). The patterned wafer was post-processed by etching, photoresist stripping and cutting individual electrodes with a DAD dicing saw (DISCO). The patterned gold electrode purchased from Pine research was made by screen-printing gold on a ceramic base, with a 2 mm2 diameter gold working electrode, a printed Ag/AgCl reference electrode, and a printed gold reference electrode.

The description and illustration of FIG. 4 are merely examples, and variations are contemplated to be within the scope of the present disclosure.

Figure 5:
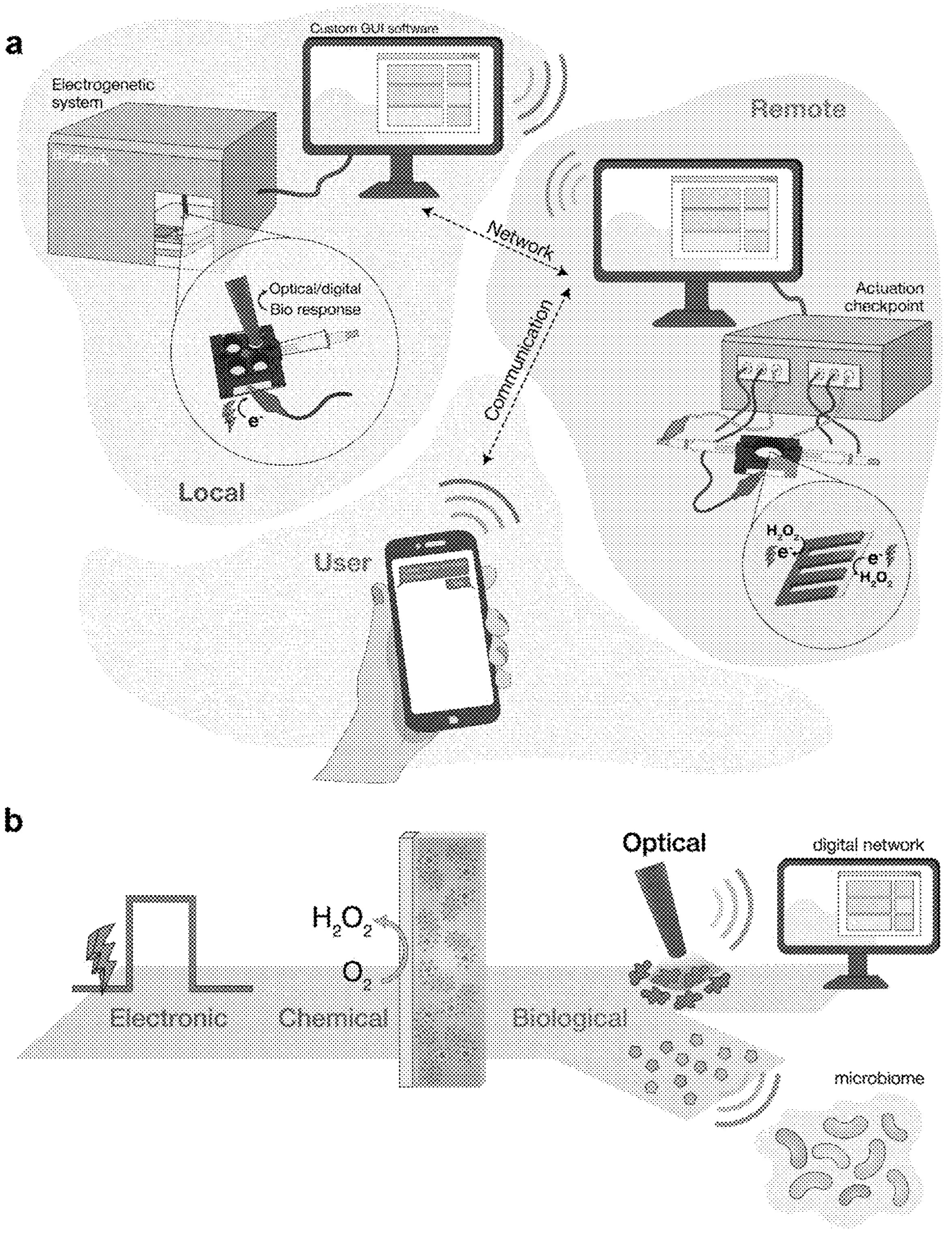
FIG. 5A-B. Information flow within the Bio-Nano Things Network.

FIG. 5A-B show information flow within a network. In FIG. 5A, electrogenetics allows direct electron flow to alter gene expression and generate digitizable optical signals for establishing connectivity with electronic systems. Information can thus be propagated within the network to other workstations and users through wireless connection enabled by the internet. The connected bio-electrochemical setup at a separate location demonstrates electronic-chemical-electronic signal conversion, through encoding electronic input into a chemical signal (peroxide) followed by biochemically decoding the chemical signal back to an electronic output. In FIG. 5B, transformation in signaling modality enables connection of biology to electronics. An encoded electronic input is first transduced to a chemical signal interpretable by biological systems to generate two different biological outputs. On top illustrates the optical signal, serving as the conduit to electronic systems after digitization. The bottom depicts QS signaling molecules that provide information to other biological systems.

Figure 17:
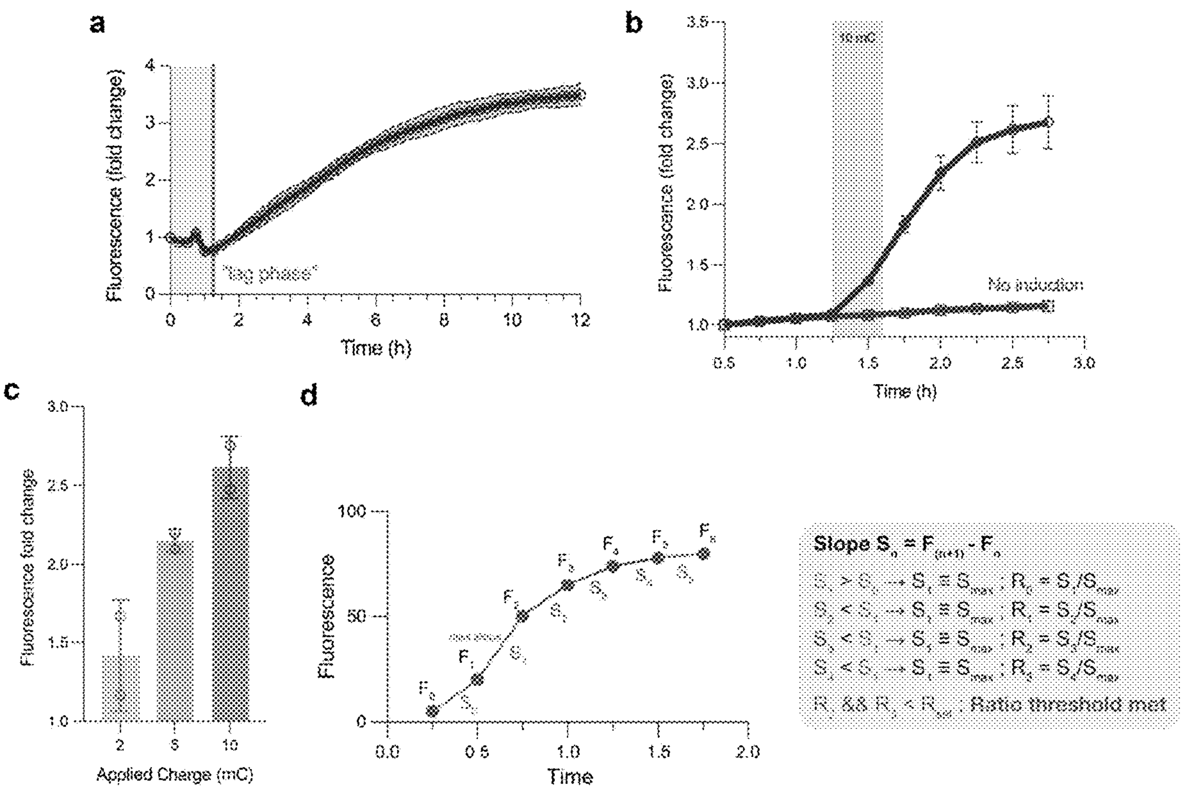
FIG. 17A-D Development of a custom algorithm to achieve dynamic control of gene expression.

FIG. 9A-C show autonomous dynamic control of gene expression via electrogenetic CRISPR. FIG. 9A shows a schematic illustration of the system allowing real-time fluorescence measurements and electrochemical induction. FIG. 9B shows an automation experiment workflow. Artificial biofilm containing engineered bacteria are assembled onto the ITO electrode of the biohybrid device. Its level of gene expression, represented by the emitted fluorescence, is constantly monitored by the Biospark system and sent to the PC (diamond) for processing. A custom algorithm (FIG. 17) then determines the status of expression via calculating the ratio of the slopes. When the user-customizable ratio threshold is met, the potentiostat is triggered to apply an induction voltage for a set time or charge. The experiment is automatically terminated when the fluorescence level is over the user-set induction level threshold. FIG. 9C shows an autonomous dynamic control of eCRISPRa-regulated gene expression. The top shows fluorescence level of the artificial biofilm containing the engineered eCRISPRa bacteria (NB101 harboring pSC-O108, pdCas9ω, and pMC-GFP). Fluorescence measurement was taken every 15 minutes (0.25 h). Experiment ended automatically when fluorescence is over the induction level threshold (blue dotted line). Brown line indicates the fluorescence level of the negative control to which no induction voltage is applied. Yellow zones indicate the periods when the induction voltage (−0.8 V) is applied. A total charge of 2 mC were applied to the cells in each zone. The bottom shows a ratio to $S_{max}$ computed by our custom algorithm. Ratio threshold (purple dotted line) was set at 0.4. The orange line indicates when the algorithm applied the initial induction voltage. Yellow lines indicate when two consecutive ratios were below set threshold, thus meeting the ratio threshold and triggering the potentiostat to apply induction voltage. The teal dotted line indicates when both the ratio threshold and the induction level threshold were met, hence no voltage was applied, and the experiment was terminated. Open circle, open square, and filled circle represent the mean and error bars represent the standard deviation of individual replicates (n=2).

Figure 10:
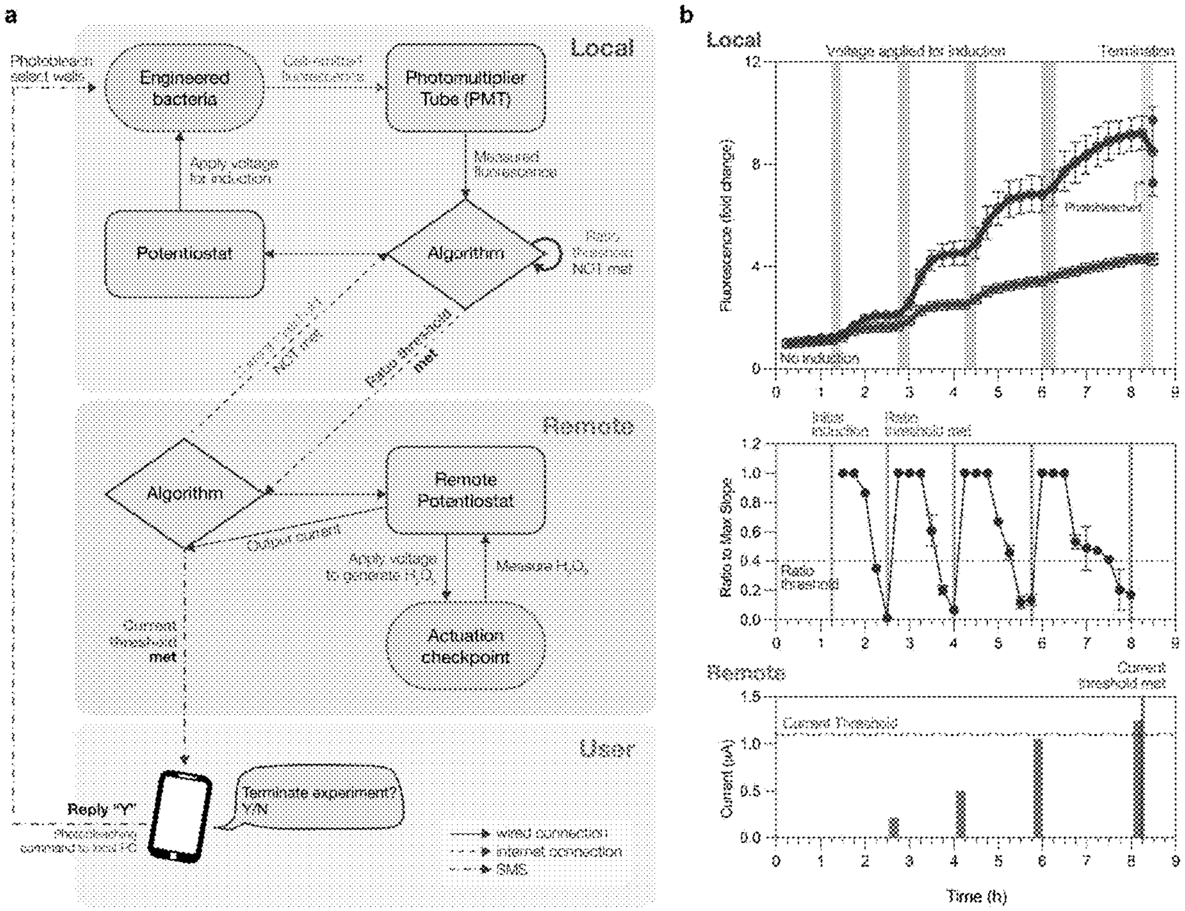
FIG. 10A-B. Network integration for establishing a Bio-Nano Things framework to enable remote feedback control of eCRISPR activity.

FIG. 10A-B show a network integration for establishing a framework to enable remote feedback control of eCRISPR activity. FIG. 10A is a system diagram of the network. FIG. 10B shows automated feedback control of eCRISPRa-regulated gene expression. FIG. 10B shows fluorescence level of the artificial biofilm containing the engineered eCRISPRa bacteria (NB101 harboring pSC-O108, pdCas9ω, and pMC-GFP). Fluorescence measurement was taken every 15 minutes (0.25 h). Open squares and line indicate the mean in fluorescence level of the negative control to which no induction voltage was applied. Zones indicate the periods when the induction voltage (−0.8 V) is applied. A total charge of 2 mC was applied to the cells in each zone. The red zone indicates when the selected sample was being photobleached. FIG. 10B also shows the ratio to $S_{max}$ computed by an algorithm. Ratio threshold (dotted line) was set at 0.4. A line indicates when the algorithm applied the initial induction voltage. Additional lines indicate when two consecutive ratios were below set threshold, thus meeting the ratio threshold and proceeding to trigger the remote 'actuation checkpoint'. FIG. 10B also shows_current threshold (dotted line) was set at 1.1 μA. A vertical line indicates when the current threshold was met, which prompted the computing device at the remote location to send a text message to users. Error bars represent the standard deviation of individual replicates (n=2).

An algorithm was built to control the 'actuation checkpoint' bio-electrochemical platform. After receiving the initiation message from the local bioelectronic system, the algorithm then commands a potentiostat at the remote location to run a pre-set program (specifically, apply −0.8 V on WE1 for 600 s, followed by 0 V on WE2 for 120s). It then compares the value of the output current to that of the user-defined current threshold: if the output current does not exceed the threshold, a message is sent to the local system to administer electroinduction right after the upcoming fluorescence measurement (for a user-defined duration or charge); otherwise, the algorithm sends a SMS message to alert the users. If 'Y' is received from the users for termination, a termination message will be sent to the local system to initiate photobleaching right after the upcoming fluorescence measurement. If 'N' is received from the users, the 'actuation checkpoint' proceeds to run the potentiostat program once more.

FIG. 17A-D show development of an algorithm to achieve dynamic control of gene expression. FIG. 17A shows a "growth curve" of engineered *E. coli* entrapped in artificial biofilm from measured fluorescence of DH5α-sfGFP cells co-deposited with PEG-SH. A "lag-phase" of approximately 1.25 hours was observed in which there was no increase in fluorescence detected, suggesting that there was no growth during this period. Open circles represent the mean fluorescence, and the dashed curves represent the error from individual replicates (n=4). FIG. 17B shows selected representation of the gene expression dynamic of in-film peroxide reporters (NEB10β+pOxy-sfGFP). A zone indicates when voltage was applied for electroinduction. The uninduced negative control is plotted. Open circles and squares represent the mean and error bars represent the standard deviation of individual replicates (n=2). FIG. 17C shows fold change in fluorescence before and after electroinduction. Bar height represents the mean and error bars represent the standard deviation (n=2). Individual replicates are indicated by the open circles. FIG. 17D shows an algorithm to monitor gene expression. Since the fluorescence was taken at a fixed time interval, the slope is defined as the difference between two neighboring fluorescence measurements. The algorithm will store and update the value of the maximum slope. It will also compute the ratio between the current slope and the maximum slope ($S_{max}$). If two consecutive ratios fall below the user-set ratio limit, the algorithm considers the ratio threshold met and will initiate electro-induction via the potentiostat. The $S_{max}$ will in turn return to 0 and start a new cycle.

More details of the algorithm are as follows.

Algorithm for AI-Control of Gene Expression

Fluorescence was taken at a fixed time interval (15 min), and the slope was defined as the difference between two neighboring fluorescence measurements.

Slope $S_n=F_{(n+1)}-F_n$

The algorithm stores and updates the value of the maximum slope ($S_{max}$) to serve as a reference point for the progression of the fluorescence level. To determine the rate of change in fluorescence levels, we took the ratio between the current slope and $S_{max}$ as described by (3).

Slope Ratio $R_{(n-1)}=S_n \div S_{max}$

If two consecutive ratios fall below the user-defined ratio limit, the algorithm considers the ratio threshold met and will initiate electro-induction by sending a command to the potentiostat. Variables such as the duration of voltage application or the total charge applied can be set in the GUI program. The $S_{max}$ will return to 0 and a new cycle will start subsequently.

The present disclosure provides a cellular system for controlling the activation, inhibition, or multiplexed control of a variety of different targets (e.g., genes-of-interest) wherein said control is mediated by electrochemical signaling within the cell and/or between a population of cells. In an embodiment, said system can be used to regulate the expression of a gene-of-interest, or for monitoring gene expression, within said cell. In an embodiment of the invention, the cell may be an engineered eukaryotic or engineered prokaryotic cell. In a specific embodiment, the cell is an engineered bacterial cell.

In one aspect, a cellular system is provided wherein cells of the system comprise constructs that place the activation or repression of gene expression, e.g., of a gene-of-interest, or a reporter gene, under the control of electrochemical signaling. Said control of expression may be mediated through the inclusion of cis-regulatory elements, such as promoters, enhancers, and silencers, which are regions of non-coding DNA, which regulate the transcription of nearby genes. For example, the gene-of-interest, or reporter gene may be cloned adjacent to a promoter that activates gene expression in the presence of an electrochemical signal. In another embodiment, the gene-of-interest, or reporter gene construct, may be cloned adjacent to a silencer that inhibits gene expression in the presence of an electrochemical signal. In specific embodiments, said cis-regulatory elements include, but are not limited to, those that are regulated by electrochemical signaling such as redox-based cell signaling.

In another aspect, the cells of the system may express trans-regulatory factors under the control of electrochemical signaling that regulate or modify the expression of distant genes by binding with the gene's target sequences, e.g., cis-regulatory elements. In such an instance, the activation or inhibition of expression of the trans-regulatory factor can result in mediation of expression of the gene-of-interest or reporter gene. In an embodiment, the trans-regulatory factor may be an inhibitor or activator of gene expression. In another embodiment, the activity of the trans-regulatory factor may be placed under the control of electrochemical signaling. In a specific embodiment, the trans-regulatory factor may be a CRISPR guide RNA (gRNA) the expression of which is mediated by electrochemical signaling. Said expressed gRNA is designed to form a complex with an engineered Cas9 transcription factor (inhibitor or activator) that is, for example, constitutively expressed within the cell. Once formed, the gRNA/Cas9 complex will then bind to the promoter region of the gene-of-interest and modulate expression of said gene.

Such a promoter/regulator cellular system includes, for example, the bacterial oxyRS regulon that is used naturally to combat oxidative stress from hydrogen peroxide. In such an instance, expression of a gene-of-interest, may be placed under the control of the oxyS promoter and the peroxide sensor, OxyR.

In an embodiment, an eCRISPR cellular system is provided for controlling the activation, inhibition, or multiplexed control of a variety of different targets, e.g., genes-of-interest. Engineered CRISPR systems contain two components: a guide RNA (gRNA) and a CRISPR-associated endonuclease (Cas9 protein). Said Cas9 protein, for use in the presently disclosed eCRISPR cellular system, include those Cas9 proteins devoid of enzyme activity that have been engineered to act as transcription factors. Said Cas9 transcription factors may act as activators (CRISPRa) or inhibitors (CRISPRi) of gene expression. In one aspect, the Cas9 transcription activator is a transcription factor ω subunit-fused deactivated Cas9 (dCas9ω). In another aspect, the Cas9 transcription inhibitor is a repurposed dCas9ω for inhibition. The gRNA is a short synthetic RNA composed of a scaffold sequence necessary for Cas9-binding and a user-defined ~20 nucleotide spacer that defines the genomic target to be modified. For example, the nucleotide spacer may be designed to bind to the promoter of a gene of interest. Components of the eCRISPR system disclosed herein, e.g., Cas9 transcription factors and gRNAs, are well known in the art.

In an embodiment, the expression of the gRNA is under the control of electrochemical signaling. Thus, one can change the genomic target of the Cas9 protein, and thus expression of the target, by simply changing the nucleotide spacer sequences present in the gRNA. Accordingly, the expression of any gene-of-interest can be targeted through specific selection of a gRNA spacer sequence that will associate with Cas9 and then with the promoter of a gene-of-interest.

In a specific embodiment, expression of a gene-of-interest is mediated by the co-expression, in the cell, of a transcription factor ω subunit-fused deactivated Cas9 (dCas9ω) and a gRNA. In one aspect, a peroxide-inducible electrochemical CRISPR (eCRISPR) system for controlling genetic expression is provided by reprogramming *E. coli*'s native oxyRS regulon for combating oxidative stress from hydrogen peroxide. In such an instance, CRISPR guide RNA (gRNA) expression is placed under the control of the oxyS promoter and peroxide sensor, OxyR. To achieve CRISPR mediated activation, the transcribed gRNA forms a complex with the co-expressed transcription factor ω subunit-fused deactivated Cas9 (dCas9ω) and activates expression of the gene-of-interest.

In an embodiment, CRISPR interference (CRISPRi) and CRISPR activation (CRISPRa) may be used to either inhibit or activate gene expression through co-expression with a gRNA of choice (depending on the target gene-of-interest). Each of the technologies utilizes a nuclease-deactivated Cas9 that binds to the target genomic region and results in RNA-directed transcriptional control of the target region. In the case of CRISPRi, dCas9 may be coupled to a transcriptional repressor domain that can effectively silence expression of one or more endogenous genes.

In an embodiment, a system is provided wherein the electrochemical mediated signaling of gene expression can be monitored through use of a gene-of-interest encoding for a tag-labeled protein, as described herein. In this case, in the presence of an electrochemical signal, the amounts of detectable label will increase (activation) or decrease (inhibition) depending on the presence of electrochemical mediated signaling. For example, as described herein, increasing levels of peroxide may result in increased levels of the detectable label, indicating that the expression of the gene-of-interest was activated. In an embodiment, the label is a fluorescent tag. In yet another aspect, the florescent label may act as a further inducer of electrochemical signaling thereby providing a signaling loop.

In yet another embodiment, the present disclosure provides recombinant cells wherein expression of a gene-of-interest is mediated electrochemically. For example, said cells may include those into which expression vectors designed for expression of a gene-of-interest, or a reporter gene, under the transcriptional control of electrochemical signals have been introduced. Such cells include bacterial as well as eukaryotic cells. The introduced nucleic acid may be present independently of the genome of the host cell or in the state of being incorporated into the genome of the host cell.

The provided recombinant cells comprise a recombinant construct that places the activation or repression of gene expression, e.g., of a gene-of-interest, or a reporter gene, under the control of electrochemical signaling. Said control of expression may be mediated through the inclusion in the construct of cis-regulatory elements, such as promoters, enhancers, and silencers, which are regions of non-coding DNA, which regulate the transcription of nearby genes into the recombinant constructs.

In an embodiment, the recombinant construct further comprises one or more genes of interest that may be expressed under electrochemical control. Such genes of interest include those encoding a wide range of therapeutic products for use in medical genetics and biomedicine. Therapeutic proteins as defined herein are peptides or proteins Which are beneficial for the treatment of any inherited or acquired disease or which improves the condition of an individual. Particularly, therapeutic proteins are those agents that can modify and repair genetic errors, destroy cancer cells or pathogen infected cells, treat immune system disorders, treat metabolic or endocrine disorders, among other functions. Therefore therapeutic proteins can be used for various purposes including treatment of various diseases like e.g. infectious diseases, neoplasms (e.g. cancer or tumor diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired. tissue, diseases of the musculoskeletal system and connective tissue. In one aspect, the recombinant cells contain a construct that directs the co-expression of additional proteins or nucleic acids necessary for electrochemical signaling. Such proteins may include, for example, Cas9 transcription proteins and/or gRNAs.

In a specific, recombinant cells are provided that place control of endogenous gene expression under the control of the eCRISPR system as disclosed herein. Said recombinant cells comprise co-expression of a Cas9 protein, inhibitor or activator transcription factor, and a target guide RNA for targeting of the endogenous gene expression. In an embodiment, the recombinant cells may express multiple Cas9 proteins, inhibitors and activators, as well as multiple gRNAs. Where multiple layers of gene expression are utilized, multiplexed control of gene expression may be achieved allowing for electrochemical signaling quorum sensing (QS) and communication between cells.

In one aspect, the recombinant cell comprises *E. coli* 's native oxyRS regulon for combating oxidative stress from hydrogen peroxide. In such an instance, CRISPR guide RNA (gRNA) expression is under the control of the oxyS promoter and the peroxide sensor OxyR. To activate CRISPR mediated gene expression, the gRNA forms a complex with constitutively-expressed dCas9ω (CRISPRa) to activate transcription of the gene-of-interest. In such an embodiment the guide RNA is designed to bind to a promoter of interest. In another embodiment, for inhibition of gene expression, the dCas9ω may be reengineered to CRISPR inhibition of gene expression.

Another aspect of the present disclosure pertains to nucleic acids encoding the gene-of-interest, or a reporter gene, wherein expression of said gene-of-interest or reporter gene is mediated by electrochemical signaling. Nucleic acid constructs may also include those encoding for Cas9 protein (inhibitor or activator transcription factors) and gRNAs of interest. Such nucleic acids may be introduced into a variety of different expression vectors, including for example, bacterial, and eukaryotic expression vectors for expression of the gene-of-interest, or reporter gene.

When the preparation method is through recombinant DNA technology, the expression vector may be a nucleic acid in the form of a plasmid, a cosmid, a phagemid, a phage, a viral vector or the like. Depending on the host microorganism, an appropriate vector may be purchased among commercially available vectors or may be used after being purchased and modified. For example, when *Escherichia coli* is used as the host microorganism, pUC19, pSTV28, pBBR1MCS, pBluscriptII, pBAD, pTrc99A, pET, pACYC184, pBR322, pJE101, pJE102, pJE103, etc. may be used. The expression vector may further include a selectable marker gene. The selectable marker gene is a gene encoding a trait that enables selection of a host microorganism containing such a marker gene and is generally an antibiotic resistance gene. For expression vector construction including recombinant DNA technology, reference may be made to Sambrook et al., Molecular Cloning, A Laboratory Manual, Cold Spring Harbor Laboratory Press, (2001), F M Ausubel et al, Current Protocols in Molecular Biology, John Wiley amp; Sons, Inc. (1994), and Marston, F (1987) DNA Cloning Techniques) and the like. All of the documents cited in the present specification are incorporated by reference in their entirety.

Methods of transforming the expression vectors into a host cell are also known in the art, and any of the known methods may be selected and used. For example, when the host cell is prokaryotic cells such as *Escherichia coli*, the transformation may be carried out through a $CaCl_2$ method, a Hanahan method, an electroporation method, a calcium phosphate precipitation method, or the like, and when the host cell is eukaryotic cells such as yeast or mammalian cells, a microinjection method, a calcium phosphate precipitation method, an electroporation method, a liposome-mediated transfection method, a DEAE-dextran treatment method, a gene bombardment method, or the like may be used. Regarding details of the transformation method, reference may be made to (Cohen, S. N. et al., Proc. Natl. Acad. Sci. USA, 9:2110-2114 (1973); Hanahan, D., J. Mol. Biol., 166:557-580 (1983); Dower, W. J. et al., Nucleic. Acids Res., 16:6127-6145 (1988); Capecchi, M. R., Cell, 22:479 (19800; Graham, F. L. et al., Virology, 52:456 (1973); Neumann, E. et al., EMBO J., 1:841 (1982); Wong, T. K. et al., Gene, 10:87 (1980); Gopal, Mol. Cell Biol., 5:1188-1190 (1985); Yang et al., Proc. Natl. Acad. Sci., 87:9568-9572 (1990); Maniatis et al., Molecular Cloning: A Laboratory Manual, Cold Spring Harbor Laboratory (1982); Hitzeman et al., J. Biol. Chem., 255, 12073-12080 (1980); and Luchansky et al Mol. Microbiol. 2, 637-646 (1988), etc.)

The host cell that may be used for transformation in the method of the present disclosure may be prokaryotic or eukaryotic cells. As the prokaryotic cells, any gram-positive bacteria and gram-negative bacteria may be used. In a specific embodiment, *Escherichia coli* is used. In order to optimize expression and maintain the functions of the gene product of interest in *Escherichia coli*, the cell may have impaired protease activity.

The host cell transformed above is cultured, thus producing the gene product of interest. The culture of the transformed host cell may be performed through any method known in the art. As the medium used for cell culture, any of a natural medium and a synthetic medium may be used, so long as it contains a carbon source, a nitrogen source, a trace element, etc. which may be efficiently used by the transformed host cell. When animal cells are used as host cells, Eagle's MEM (Eagle's minimum essential medium, Eagle, H. Science 130:432 (1959)0, α-MEM (Stanner, C. P. et al., Nat. New Biol. 230:52 (1971)), Iscove's MEM (Iscove, N. et al., J. Exp. Med. 147:923 (1978)), DMEM (Dulbecco's modification of Eagle's medium, Dulbecco, R. et al., Virology 8:396 (1959)) or the like may be used. Regarding details of the medium, see, for example, R. Ian Freshney, Culture of Animal Cells, A Manual of Basic Technique, Alan R. Liss, Inc., New York.

In still another aspect, a method is provided of preparing a gene product of interest in a cell wherein expression of the gene product of interest is under the control of electrochemical signaling. The preparation method comprises (i) culturing the recombinant cells as described herein; (ii) providing an electrochemical signal; and (iii) allowing for expression of the gene product of interest. In a further step, the gene product of interest is purified from the cell.

Example 1

Material and Methods

Chemicals

Potassium chloride (KCl), $H_2O_2$ (30%), phosphate buffered saline (PBS), potassium phosphate monobasic, potassium phosphate dibasic, potassium hexachloroiridate(III) ($K_3IrCl_6$, Ir), and gelatin from porcine skin (gel strength≈175 g Bloom, Type A, G2625) were purchased from Millipore-Sigma. All antibiotics (ampicillin, kanamycin and chloramphenicol) were purchased from Millipore-Sigma. Lysogeny broth (LB) and agarose were from Fisher Scientific. Fluorescent beads and Pierce® horseradish peroxidase (HRP) were purchased from Thermo Fisher Scientific. 4-arm PEG-SH (MW 5000) were from JenKem USA. 1,1'-Ferrocene dimethanol (FcN) was from Santa Cruz Biology. AI-1 (N-3-oxo-dodecanoyl-L-Homoserine lactone) was from Cayman Chemicals. Ir, FcN, and AI-1 were initially prepared as 20 mM, 1 M, and 1 mM DMSO stocks, respectively.

Culture Media and Conditions

Unless otherwise indicated, cells were grown overnight in LB at 37° C., 250 r.p.m. shaking, inoculated at $OD_{600}$=0.1 in LB media the following day, and grown until the indicated cell density (optical density at 600 nm, $OD_{600}$). Optical density was measured using an UV-Vis Spectrophotometer (Beckman Coulter).

Plasmid Construction

All bacterial strains and constructs used in this study were listed in Table 1. All enzymes, competent cells and reagents were from New England Biolabs and used according to provided protocols. Q5 polymerase and primers in Table 3 (gene sequences in Table 2) were used for PCR reactions. DpnI digestion, polynucleotide kinase phosphorylation, T4 ligations, Gibson assembly and *E. coli* chemical transformation were performed using New England Biolabs product protocols. DNA clean-up (Zymo Research), gel extraction (Zymo Research) and plasmid preparation kits (Qiagen) were performed using provided protocols. Synthetic gene fragment containing the multiplex crRNAs was purchased from Thermofisher Scientific. Synthetic gene fragment containing the 108 spacer and gRNA scaffold was purchased from Integrated DNA Technologies (IDT). Synthetic gene fragment containing tracrRNA was purchased from Integrated DNA Technologies (IDT).

Electrodeposition of *E. coli* and PEG-SH

*E. coli* grown to mid-log phase were harvested via centrifugation at 3000 rcf for 10 minutes, then resuspended in 1×PBS to 2× the desired OD. To prepare the 2×PEG-SH solution, 100 mg/mL of PEG-SH were dissolved in phosphate buffer (PB) containing 10 mM FcN. Prior to electrodeposition, the two solutions were mixed at a 1:1 ratio. We then performed chronoamperometry, poised at 0.8 V for 30s, to initiate oxidation of the thiol group for crosslinking. The endpoint charge was recorded for each run. Excess cell/PEG-SH solution was then removed, and the generated film was carefully washed with PBS to remove any unbound cell/PEG-SH.

Fluorescence Microscopy

Composite fluorescence images were obtained using a ZEISS LSM700 confocal microscope Quantification of Film Thickness Overnight culture of DH5α-sfGFP was harvested via centrifugation (3000 rcf, 15 min) and resuspended in PBS to $OD_{600}$=12/mL. 2×PEG-SH solution was prepared as previously stated and was mixed 1:1 with the *E. coli* solution. 100 μL of cell/PEG-SH mixture were loaded into the wells of our ITO-based electronic device and electrodeposition (0.8 V) was performed for the indicated duration. After decanting the excess solution and thorough washing, a ZEISS LSM700 confocal microscope was used to obtain Z-stack images of the generated film.

Peroxide Generation and Quantification

Electrochemical peroxide generation was performed in the biohybrid electronic device with its setup as described above. 150 μL of 20% LB mixed with 80% PBS (20% LB) was added into each well (surface area=(x) $mm^2$). The working electrode solution was undisturbed (or, where indicated, stirred via blowing $O_2$ into the wells). The electrodes were connected to a potentiostat (either 700-series CH Instruments or a custom FPGA-based potentiostat). Chronoamperometry, poised at −0.8 V for the indicated duration, was performed to generate hydrogen peroxide. The endpoint charge was recorded for each run.

To quantify the generated peroxide, we used the Pierce® quantitative peroxide assay kit (aqueous) (Thermo Fisher Scientific) according to the manufacturer's instructions. Briefly, the working reagent was prepared by mixing one volume of Reagent A with 100 volumes of Reagent B, with at least 200 μl prepared for each sample to be assayed. Ten volumes of the working reagent were added to one volume of sample (typically 200 μl working reagent to 20 μl sample) in a well of a clear-bottomed 96-well plate. The reaction was mixed and incubated for 15-20 min, after which a Spark® microplate reader (Tecan) was used to measure the absorbance at 595 nm. Sample peroxide concentration was calculated by comparison with a standard curve (dilutions of 30% peroxide) performed the same day.

General and Co-Culture Electroinduction Set-Up

Electroinduction experiments were performed in the custom biohybrid electronic device. Deposition of the cell/PEG-SH film was performed as described in previous sections. After thorough washing to remove excess cell/PEG-SH solution, 150 μL of 20% LB was added to each well as the culture media. Peroxide was generated via chronoamperometry as described in sections above, with voltage application for a specified duration (e.g., 1800 s). The biohybrid device was then moved to an incubator (30 or 37° C., as indicated) for incubation. For all automated experiments, the biohybrid device remained in a custom-made environmental chamber inside the Biospark system with temperature (34° C.) and humidity (≥80%) control. 0.4 $ft^3$/h (scfh) of oxygen was supplied during electroinduction for media perturbation and oxygen supply to generate sufficient peroxide.

Samples (i.e., the media immersing the film) were removed at indicated time intervals and sterile filtered for downstream bioassays. For coculture experiments, AI-1 responsive strain (NEB10β+pLasR_S129T-GFPmut3) that were grown to mid-log phase were inoculated to an OD600 of 0.025 in 20% LB, then added into the wells containing the generated 'artificial biofilm' for electroinduction.

Fluorescence Measurements

Unless stated otherwise, a Spark® plate reader (Tecan) was used to measure GFP fluorescence with excitation/emission wavelengths of 488/520 nm. For dynamic gene expression control experiments, GFP fluorescence was measured using our custom-built Biospark platform, as described in sections below.

AI-1 Quantification

AI-1 quantification was performed by bioluminescence assay. AI-1 reporter cells JLD271 pAL105 were grown overnight in LB at 37° C. and 250 r.p.m. shaking with the appropriate antibiotics. The following day, AI-1 solutions (0-84 nM) for the standard calibration curve were prepared in 20% LB. The reporter cells were diluted 500-fold in LB with the appropriate antibiotics. For every experimental replicate, 90 μl of diluted reporter cells and 10 μl of the standard AI-1 solutions were added into the wells of a white-bottom 96-well plate (Corning). Experimental conditioned media samples were prepared similarly after sterile filtering and diluting between two- and thousand-fold to maintain a linear assay range. Microplate with reporter cells and conditioned media samples were incubated at 30° C. and 250 r.p.m. shaking in a Tecan® microplate reader, and its luminescence was measured by the plate reader every 30 minutes for 3-5 hours. The AHL concentration of each sample was calculated using the standard curve.

RT-qPCR

NB101 harboring the plasmids that allow CRISPR activation of GFP (pSC-O108+pdCas9ω+pMC-GFP) were grown at 37° C. and 250 r.p.m in LB overnight. The following day, overnight cultures were diluted to OD600=0.1 and grown at 37° C. and 250 r.p.m until reaching mid-log phase. Peroxide stock solution (10 mM) were then spiked into the cultures to induce the expression of sgRNA. After incubation, samples were collected via centrifugation. Total and microRNA were extracted using a miRNeasy Kit (Qiagen) and quantified using a Nanodrop (Thermo Scientific). RT-qPCR was then carried out using the Power SYBR™ Green RNA-to-CT™ 1-Step Kit (Applied Biosystems) and a Quantstudio 7 Flex Real-time PCR system (Applied Biosystems).

AI-2 Activity Assay

Relative AI-2 levels were determined using the *V. harveyi* reporter BB170 bioluminescence assay[11] with slight modifications. AI-2 reporter cells BB170 were grown overnight in AB media at 30° C. and 250 r.p.m shaking with appropriate antibiotics. The following day, overnight BB170 culture was diluted 5000-fold in AB media. For every experimental replicate, 180 μl of diluted BB170 culture and 20 μl of conditioned media were added into the wells of a white-bottom 96-well plate (Corning). The microplate was then incubated at 30° C. and 250 r.p.m. shaking in a Tecan® microplate reader, and its luminescence was monitored by the plate reader every 30 minutes after 3-hour incubation. AI-2 activity was calculated by dividing the RLU produced by the reporter after addition of conditioned media by the RLU of the reporter when growth medium alone was added.

Electrodeposition of HRP/Gelatin Hydrogel and Electrochemical Detection of $H_2O_2$ The protocol for HRP/gelatin deposition and electrochemical detection of peroxide as described by Li et al. was used with slight modifications[7]. Deposition of HRP/gelatin was performed on a custom patterned electrode generated through laser-cutting the ITO-coated glass slide into two separate interweaving working electrodes. This zig-zag pattern was chosen to ensure the generated peroxide be at the vicinity of the deposited HRP/gelatin hydrogel for detection. A custom 3D-printed housing with one central well exposing the working electrodes and two side openings for the insertion of Ag/AgCl reference electrodes was then attached to the patterned ITO electrode (FIG. 19A-C). A custom connector attached with two Pt wires provided the 3-electrode system with counter electrodes. Upon deposition, a solution containing HRP (1 mg/mL), gelatin (25 mg/mL), and 5 mM Ir) was pipetted into the central well of the device followed by applying an oxidative voltage (+1.2 V) for 2 minutes on working electrode 2 (WE2). After removing the excess HRP/gelatin, a solution of 0.25 mM FcN in 0.1 M phosphate buffer was added into the well submerging both working electrodes. Electrochemical peroxide generation was performed on working electrode 1 (WE1) by applying −0.8 V for the desired duration. To detect the peroxide generated from WE1, a constant voltage (0 V vs Ag/AgCl) was imposed on WE2 for 120 s, and the current output was recorded (FIG. 19E).

Cloning of Peroxide-Inducible gRNA Expression Plasmids (Supplementary)

Plasmid pSC-O108 (Table 1) for peroxide-inducible expression of sgRNA sg108 was made via PCR amplification and Gibson assembly. First, pSC-108gRNA2 was removed of soxR, soxRS promoter region, and sgRNA sg108 by restriction digestion with ClaI and BamHI. Gene fragment containing oxyR and oxyS promoter (Table 2) was amplified from plasmid pOxy-LacZlaa[3] with primers SW01 and SW02 (Table 3). After DpnI treatment, fragments were ligated by Gibson Assembly. Next, gene fragment containing spacer 108 and gRNA scaffold was then PCR amplified with primers SW03 and SW04 and inserted into the linearized intermediate product via primers SW05 and SW06 to generate the construct pSC-O108.

Plasmid pSC-LuxS1 for peroxide-inducible expression of sgRNA LuxS1 was made via site-directed mutagenesis. Spacer 108 (Table 2) in plasmid pSC-O108 was swapped with LuxS1 (Supplementary Table 2) using primers 7 and 8.

Plasmid pSC-sg108+LuxS1 for peroxide-inducible expression of crRNAs spacer 108 and LuxS1 was made via PCR linearization, restriction digestion, and T4 ligation. pSC-O108 was initially PCR linearized using primers SW09 and SW10 to remove the spacer 108 and the gRNA scaffold, as well as adding restriction sites BamHI and XhoI. Gene fragment containing crRNAs spacer 108 and LuxS1 (Table 2) was inserted into linearized pSC-O108 backbone via restriction digestion and T4 ligation. After this, the gene fragment containing the tracrRNA (Table 2) was inserted into the product generated from the previous step via restriction digestion and T4 ligation to generate the final construct.

Cloning of pLuxS1

Plasmid pLuxS1 for constitutive expression of sgRNA LuxS1 was constructed via site-directed mutagenesis using primers 11 and 12 to swap the spacer 108 in plasmid pS108gRNA[2] to LuxS1.

Cloning of pMC-lasI-LAA

Plasmid pMC-lasI-LAA was constructed via PCR amplification and Gibson assembly. pMC-GFP[2] was linearized and removed of GFPmut2 by primers SW13 and SW14. Primers SW15 and SW16 were used to amplify and add the LAA ssRA tag to lasI. lasI with the added LAA tag was then inserted to the linearized backbone via Gibson assembly.

Cloning of pOxy-sfGFP-AAV (Supplementary)

Plasmid pOxy-sfGFP-AAV was constructed via site-directed mutagenesis using primers 17 and 18 to add the AAV ssRA tag to pOxy-sfGFP[24].

Results

Figure 6:
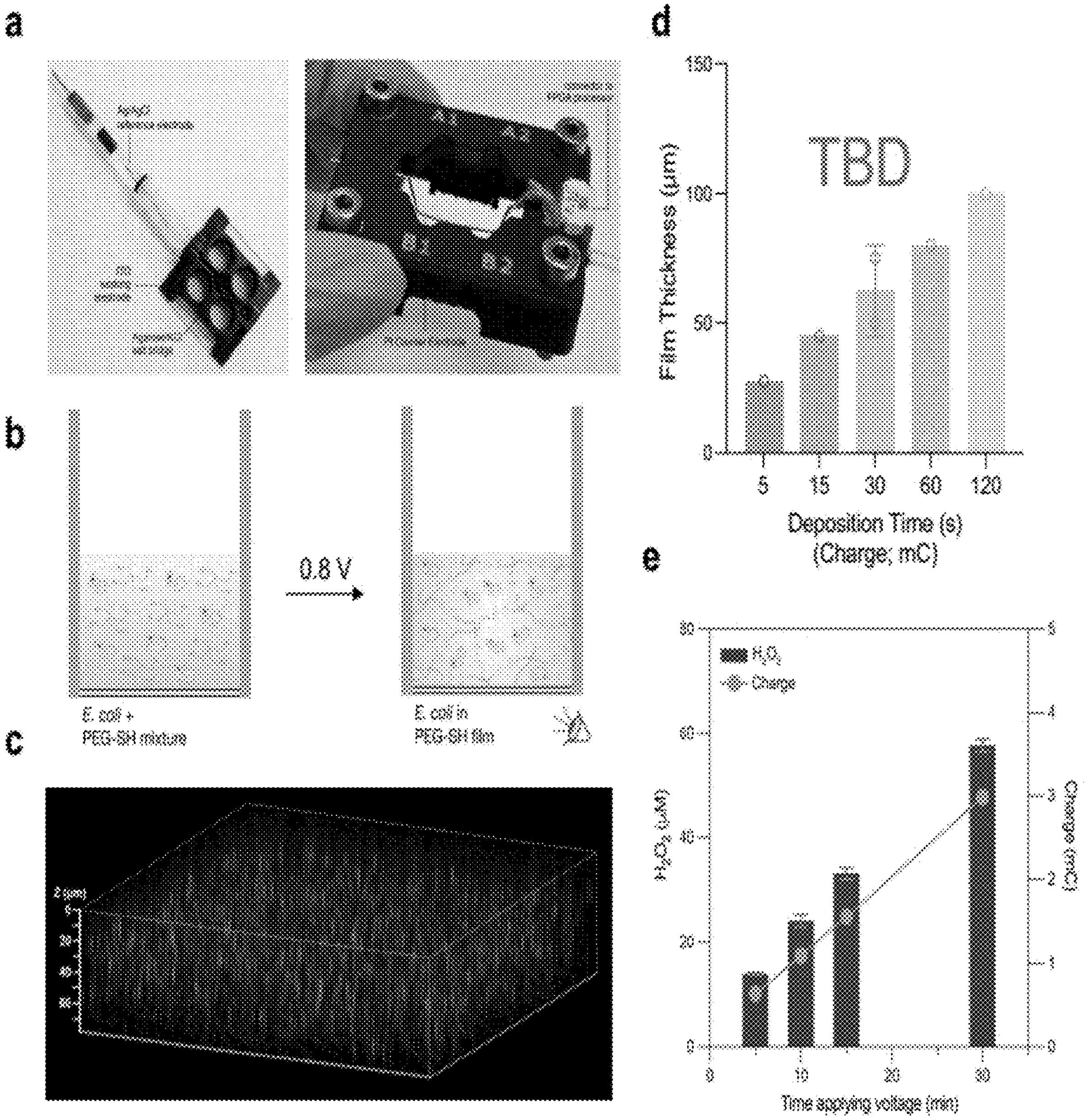
FIG. 6A-E. The making of an "Artificial Biofilm" and integration with a biohybrid electronic system.

Controllable Hydrogel Deposition for Immobilizing *E. coli* to Integrate with Biohybrid Device To better integrate biological systems that were mostly cultured in a suspension aqueous state with electronic devices, inspiration was taken from bacterial biofilms found in nature and created an 'artificial biofilm' to immobilize electrogenetic *E. coli* onto an electrode. Due to the diffusion-limiting nature of peroxide, this also greatly benefits the signal transfer by localizing the cells at the bioelectronic interface[3]. The 'artificial biofilm' was generated through electrodepositing the electrogenetic bacteria with thiolated polyethylene glycol (PEG-SH) to form a cell-containing hydrogel. Specifically, cells were mixed with PEG-SH monomer in a solution containing a redox mediator ferrocene (FcN) to facilitate the oxidation of thiol groups in PEG-SH to form disulfide bonds (FIG. 6A). When applied an oxidative voltage, PEG-SH began to crosslink, forming a film to entrap the cells within the matrix. This method was initially established by Li et al., and successful entrapment of living cells had been demonstrated without compromising the cells' viability[7]. In this work, cell/PEG-SH co-deposition was further characterized and it was shown that the 'artificial biofilm' can be robustly deposited in a controlled manner. First, electrodeposition of the 'artificial biofilm' can be spatially controlled. As shown by the representative composite fluorescence images (FIG. 6B), PEG-SH hydrogel containing engineered *E. coli* that constitutively express GFP (DH5α-sfGFP) were homogeneously deposited on patterned gold/ITO (?) electrodes with surface areas ranging from ~13 mm2 to 100 mm2, and the cell distribution was clearly defined by the geometry of the electrode. The number of deposited cells also correlated with the size of the electrode (FIG. 6C), suggesting it is possible to guide (AI-2 assay probably). Second, 'artificial biofilms' can be controllably deposited with custom thickness by varying the deposition time. To enable optical observations, the film containing DH5α-sfGFP was deposited on an indium tin oxide (ITO) electrode and took confocal Z-stack images to estimate its thickness (FIG. 6D). The results showed that film thickness, along with the deposited cell count, highly correlated to deposition time and charge (FIG. 6E). This provided an orthogonal approach to precisely control the characteristics of this living material.

Figure 11:
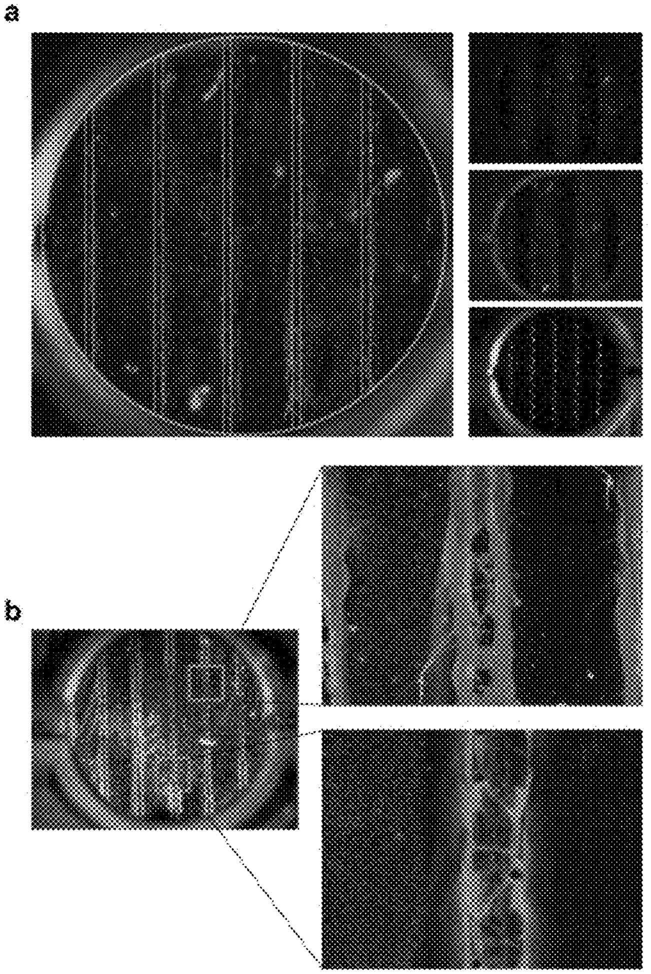
FIG. 11A-B. Spatially controlled biofilm generation (FIG. 11A) Fluorescence beads and PEG-SH co-deposition. Left: Merged microscopy image of three images taken under green, red fluorescence filters, and in brightfield. The white circle indicated the edge of the well, and the white lines indicated where the ITO glass was cut. Right: Individual microscopy images. From top to bottom were images taken under a green fluorescence filter, a red fluorescence filter, and in brightfield, respectively.

We also created an ITO-based electronic device to serve as the experimental platform in the study. Following a typical 3-electrode setup, ITO-coated glass was chosen as the working electrode (WE) due to its transparency for optical observations and measurements. A 3D-printed housing was attached to the ITO electrode to generate separate wells with similar dimensions to a conventional 96-well plate. The device's ability to generate peroxide via electronic input was tested. Although previous studies reported that peroxide can be generated by applying voltages ranging from −0.3 to −0.9 V (versus Ag/AgCl) to partially reduce oxygen[8] (according to reaction $O_2+2H^++2e \leftrightarrow H_2O_2$), we found that biasing the ITO electrode to −0.8 V produced the highest level of peroxide (FIG. 11). Consistent with previous reports, oxygen reduction to peroxide was stoichiometrically proportional to applied charge. Altogether, a biohybrid device was built consisting of a living 'artificial biofilm' and an electronic platform capable of generating peroxide to provide as a transduction mechanism to enable electrogenetic regulation.

oxyRS-Based Electrogenetics CRISPR Activation

Figure 7:
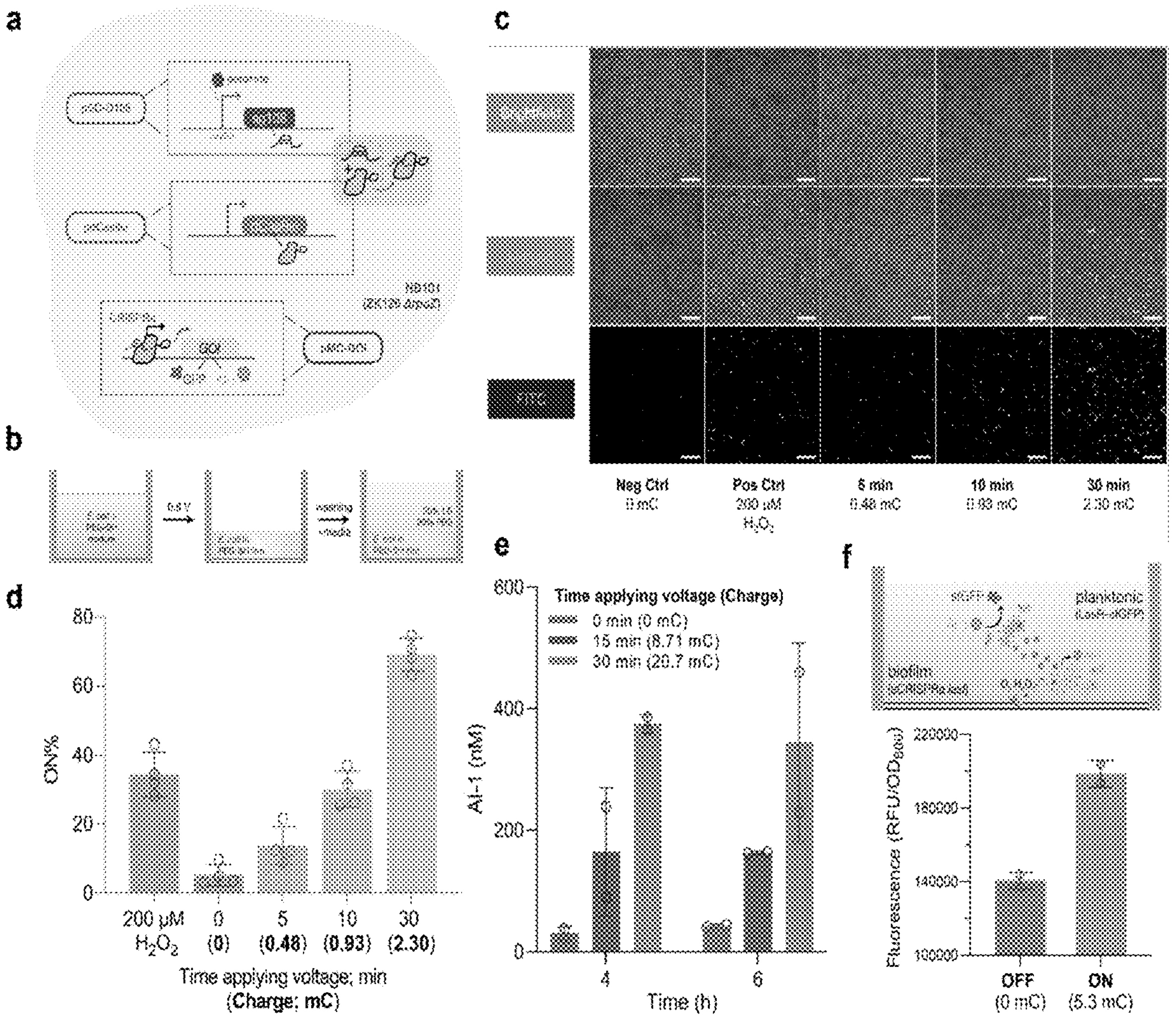
FIG. 7A-F. Demonstration of a tunable eCRISPRa on an "artificial biofilm" (FIG. 7A) Schematic illustration of the electrogenetic CRISPRa system powered by the oxyRS regulon. Electro-induced gRNA sg108 (pSC-O108) forms a complex with constitutively-expressed dCas9ω to initiate transcription of the gene-of-interest (GOI) in plasmids pMC-GFPmut2 or pMC-LasI-LAA.
Figure 12:
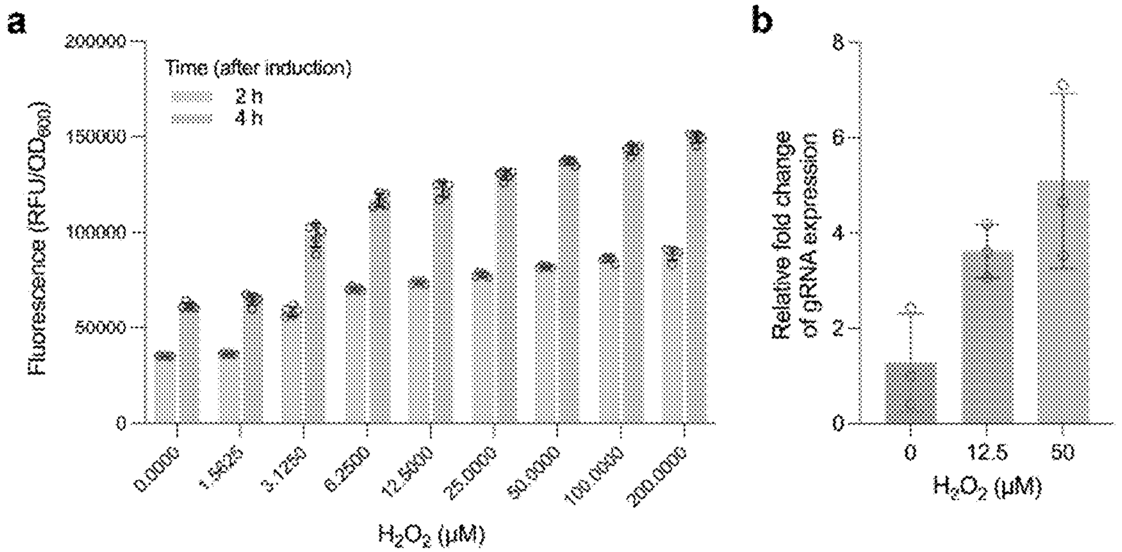
FIG. 12A-B.

In hopes of expanding the oxyRS-based electrogenetics toolbox, a versatile CRISPR transcriptional regulation system was developed to allow activation, repression, and multiplexed regulation of genes at the transcription level. Here, a peroxide-mediated, electrically-inducible CRISPR transcriptional activation (CRISPRa) system was created by rewiring the previously developed soxRS-based electrogenetic CRISPR (eCRISPR)[2] and placing the single guide RNA (sgRNA) under the control of oxyS promoter (FIG. 7A). To monitor CRISPRa performance, plasmid pMC-GFP was used in which the expression of reporter gene gfpmut2 would be upregulated by the CRISPR components. First, it was confirmed in liquid culture that both CRISPR activation of GFP and sgRNA's expression level were peroxide-inducible (FIG. 12A-B). Next, we sought to test the electroinduction of CRISPRa using the biohybrid device (FIG. 7B). NB101 cells harboring the tunable CRISPRa plasmids (pSC-O108, pdCas9ω, and pMC-GFP) were grown to mid-log phase and assembled into an 'artificial biofilm' with an $OD_{600}$ of 1/mL. In FIG. 7C and FIG. 7D, it was found the percentage of cells displaying CRISPRa-mediated fluorescence (ON %) increased as a function of the duration of voltage (−0.8 V) application and charge 4 hours after electroinduction. With 10 minutes of electroinduction, CRISPRa GFP levels (30%) were on par with a 200 μM peroxide exogenously-induced control (34%), while 30 minutes of electroinduction resulted in ~70% of cells exhibiting CRISPRa activity.

Figure 8:
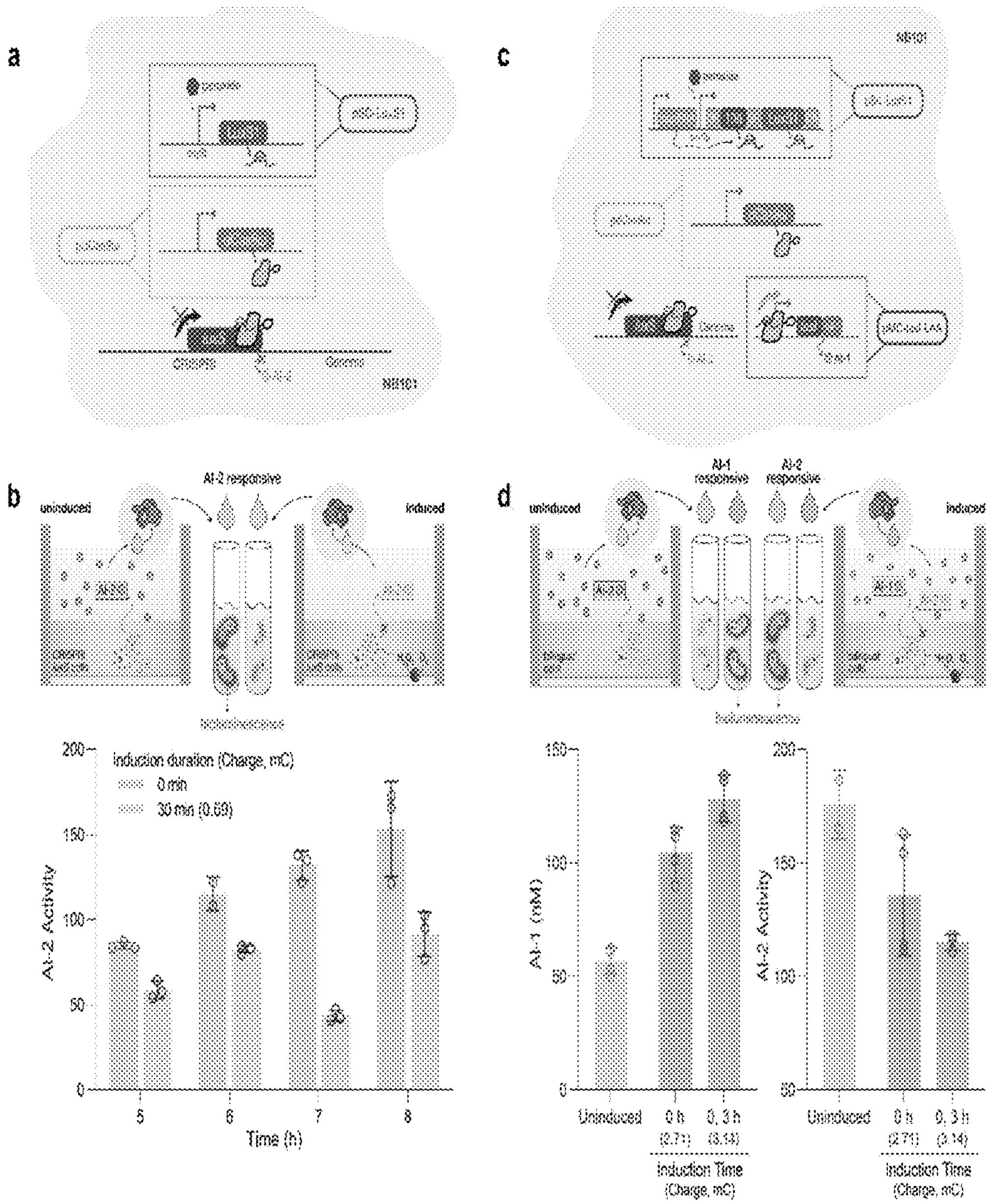
FIG. 8A-D. eCRISPR inhibition of a native QS signal and multiplexed control of QS communication.
Figure 13:
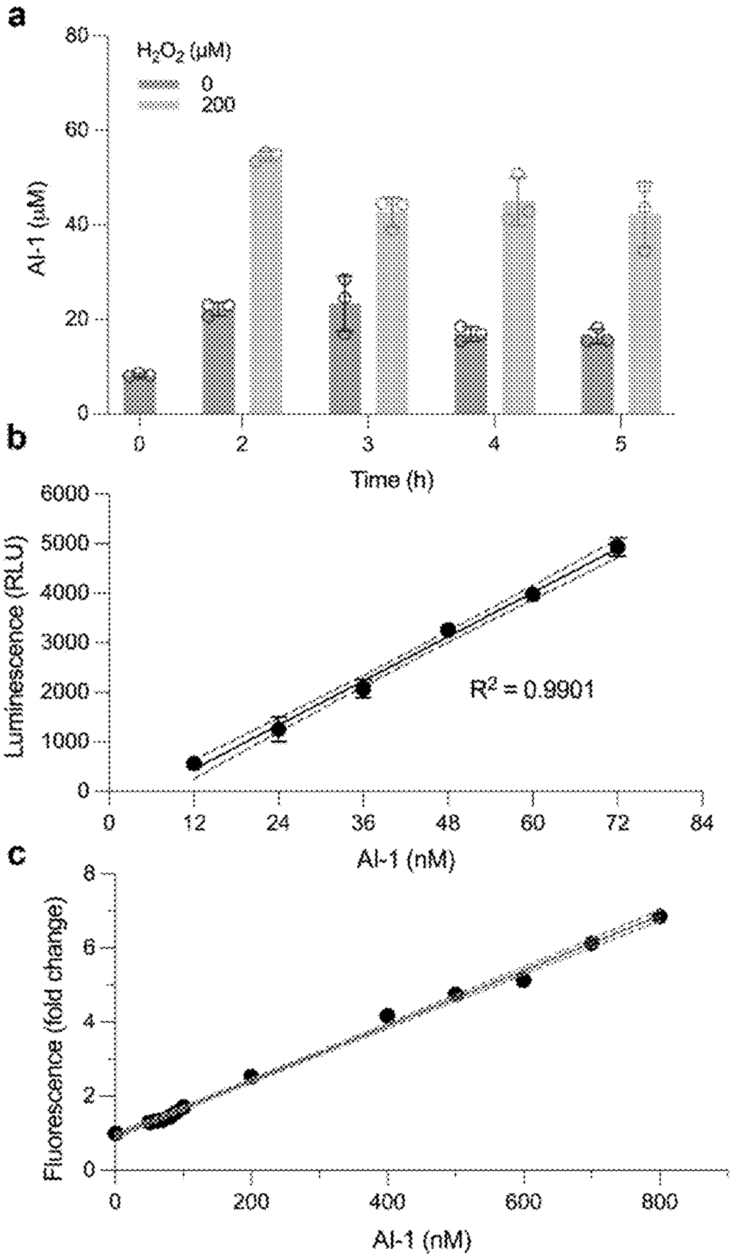
FIG. 13A-C. 11202-inducible CRISPR activation of lasI (FIG. 13A) AI-1 produced by NB101 harboring pSC-O108, pdCas9ω, and pMC-lasI-LAA after being induced by 0 μM (blue) and 200 μM (yellow) of $H_2O_2$. Error bars represent the standard deviation (n=3). Open circles represent individual replicates.
Figure 14:
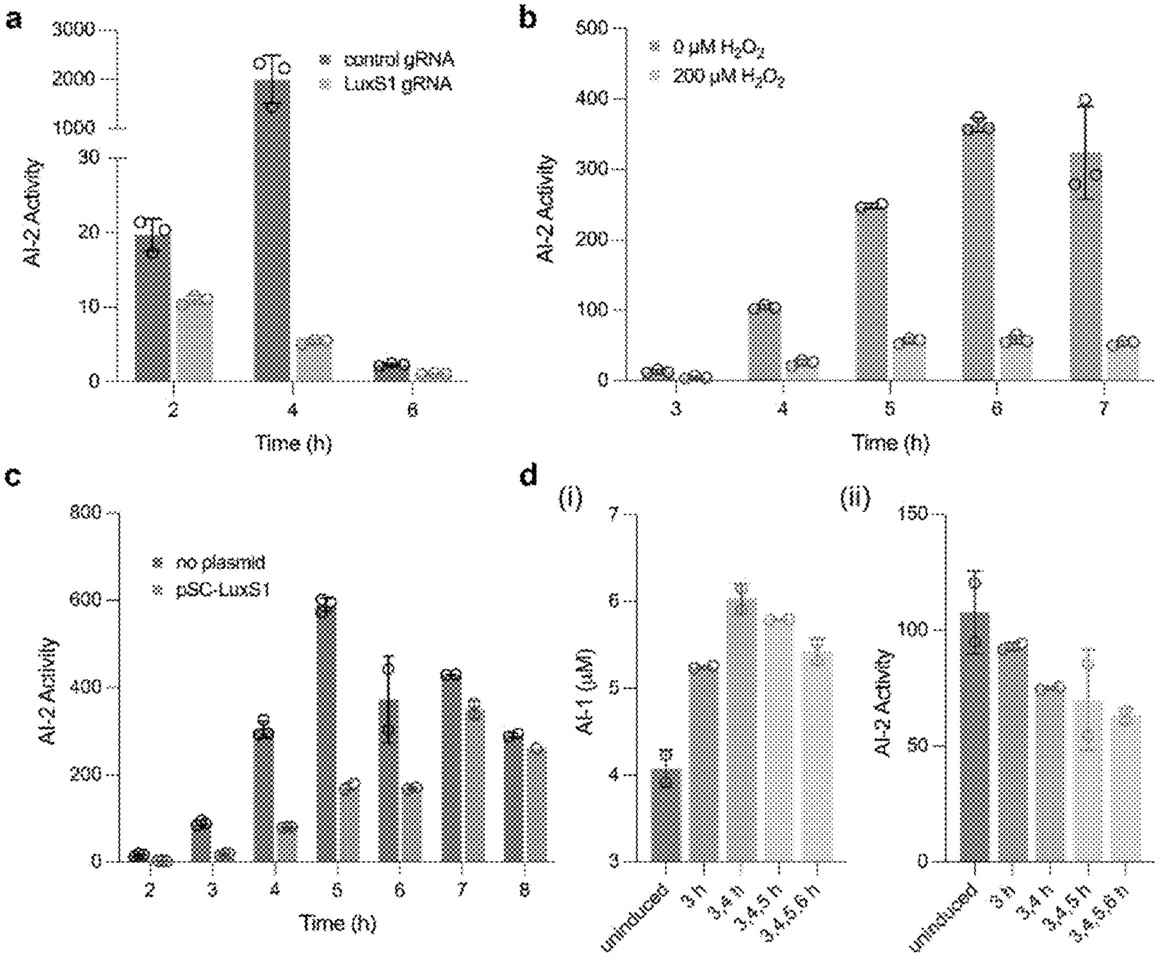
FIG. 14A-D. $H_2O_2$-inducible luxS CRISPRi and multiplexed control of QS signaling.
Figure 15:
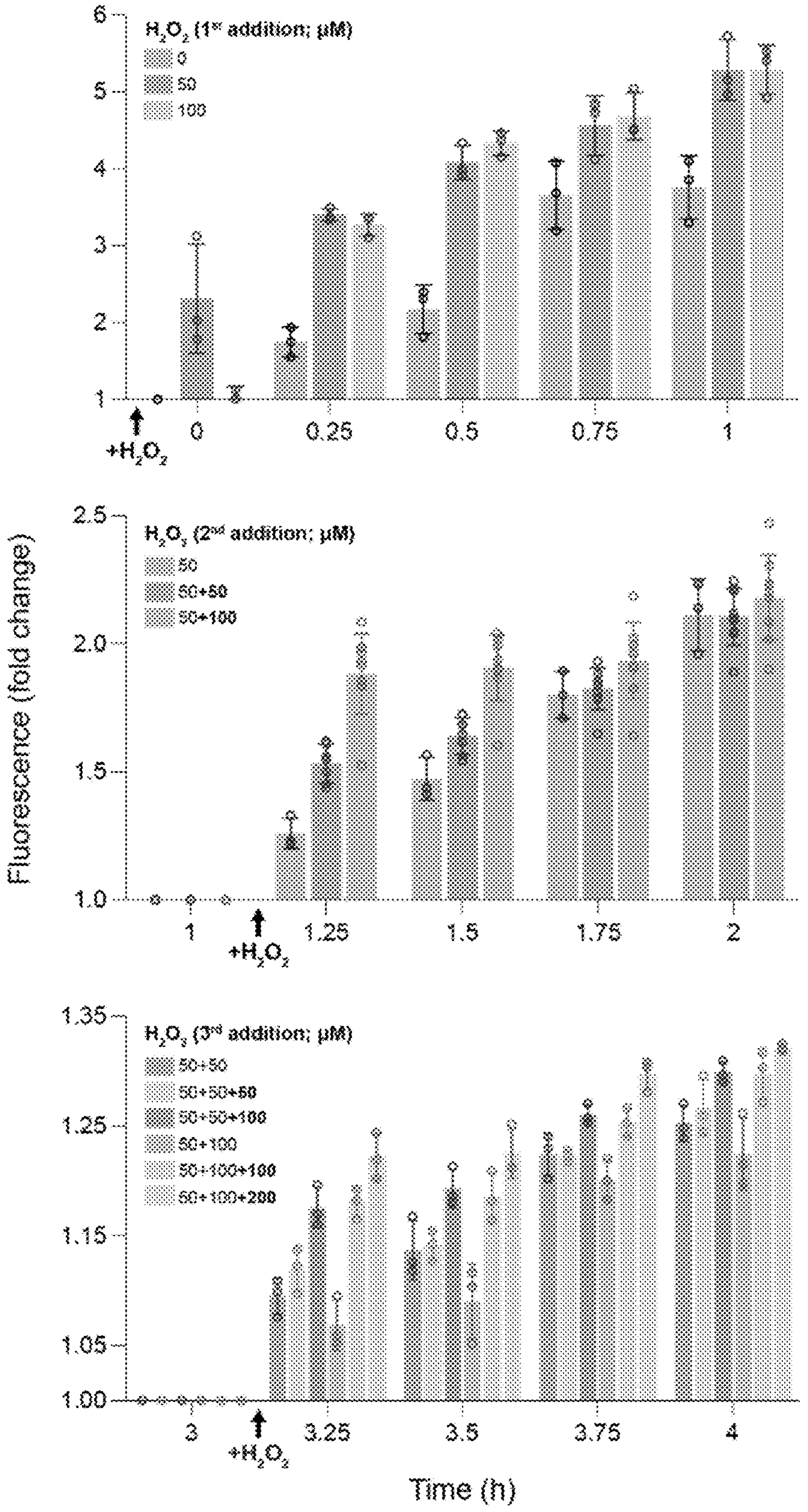
FIG. 15. $H_2O_2$-induced gene expression is temporal and can be dynamically controlled. Measured Fluorescence from peroxide-reporter cells (NEB10β+pOxyRS-sfGFP-AAV). Cells were harvested at OD=0.4 via centrifugation and re-inoculated in 20% LB. Peroxide was added to each sample at indicated times. For the data in time points 0-1 h, fluorescence was normalized to the fluorescence of the uninduced control at time 0. For data in time points 1-4 h, fluorescence was normalized for each sample's fluorescence at the beginning of each cycle (i.e., 1 or 3 h). Bar Height represents the mean, and error bars represent the standard deviation (n≥3). Individual replicates were indicated by the open circles.

Having shown that one can electrically induce CRISPRa in the biohybrid device, testing was done to demonstrate information routing between electronic to biological signaling modalities by initiating a specific QS communication (i.e., las AI-1 QS system from *Pseudomonas aeruginosa*) that is not natively found in *E. coli* through peroxide-mediated eCRISPR. A new reporter plasmid (pMC-lasI-LAA) was constructed by replacing gfpmut2 with the AI-1 producer lasI (fused with a ssRA tag), allowing CRISPRa control of AI-1 production. This new reporter plasmid, along with the other CRISPRa components (dCas9ω and pSC-O108) were transformed into NB101 cells. These populations were later referred to as CRISPRa lasI cells. Prior to electro-induction tests, CRISPRa lasI cells were also confirmed to be peroxide-inducible in liquid culture (FIG. 13A). For demonstrating on-device eCRISPRa, CRISPRa last cells (at $OD_{600}$=3/mL) were electrically induced to activate AI-1 production following the assembly onto the biohybrid device. At 4 and 6 h post-induction, media submerging the 'artificial biofilm' (i.e., conditioned media, CM) were collected and incubated with AI-1 bioluminescent reporter cells for quantitation of AI-1 concentration (FIG. 13B). Similar to the results of eCRISPRa GFP, it was found that AI-1 levels were electrically inducible and correlated to the duration of voltage application and charge (FIG. 7C). Finally, control of a second population through CRISPRa-mediated QS signal routing was demonstrated. To achieve this, CRISPRa lasI cells were assembled into an 'artificial biofilm' submerging in culture media inoculated with an AI-1 fluorescent reporter strain (NEB10β harboring plasmid pLasR_S129T-GFPmut3) (FIG. 13C). After receiving electrogenetic induction, the AI-1 fluorescent reporters in the induced co-culture (ON) exhibited higher (~1.5-fold) GFP levels compared to those in the non-induced (OFF) co-culture (FIG. 7F). In summary, on-device, peroxide-mediated eCRISPR that allows propagation of the localized electrogenetic cue across different cell populations, and coordination of population-wide behavior with the help of QS communication was demonstrated.

eCRISPR inhibition and multiplexed control of QS to enable 'multilingual' communication While it was shown that by enabling peroxide-mediated eCRISPR activation of QS can open a new a line of communication to other microbial or even mammalian populations[9,10], CRISPR transcription regulation offers additional functions such as gene repression and multiplexed control for multi-locus transcription regulation. Here, these functions were explored and applied to enable electrically-controlled 'multilingual' QS communication. In particular, the aim was to create an engineered *E. coli* that switches its 'spoken language' (i.e., QS signaling) from its 'mother tongue' (luxS-based AI-2) to a 'foreign language' (las AI-1 from *P. aeruginosa*) upon receiving the electronic signal. Unlike the las system, luxS/AI-2 QS system is found natively in many bacteria, Gram positive and negative alike, including the experiment chassis *E. coli*. To prohibit *E. coli* from secreting AI-2, a sgRNA LuxS1 was designed that is homologous to the AI-2 producer gene luxS and repurposed dCas9ω for CRISPR inhibition (CRISPRi) (FIG. 8A). The gRNA was expressed, along with a non-specific control, initially under a strong, constitutive promoter in culture to examine the efficacy of LuxS1. Compared to the control gRNA, a ~400-fold decrease in AI-2 activity was observed from the cultures that constitutively expressed LuxS1, demonstrating highly effective inhibition. Next, it was verified whether the CRISPRi system could be inducibly controlled via peroxide. For this, plasmid pSC-LuxS1 was constructed by replacing the constitutive promoter to the oxyS promoter to allow inducible expression of LuxS1. Suspension culture of NB101 cells harboring CRISPRi components (pSC-LuxS1 and pdCas9ω) were grown in 37° C. and induced with 0 or 200 μM of peroxide at OD=0.4. 0.8% (w/v) glucose was added to LB media to avoid the naturally occurring AI-2 self-uptake[12]. Similarly, the collected conditioned media samples subsequently underwent BB170 bioassay for AI-2 quantification (FIG. 14B). We found that AI-2 activity of the non-induced control was ~7-fold higher than that of the induced sample, confirming peroxide-inducible inhibition of AI-2 QS system by CRISPR inhibiting luxS. Prior to testing electrogenetic CRISPRi, the AI-2 profile of entrapped cells in the 'artificial biofilm' was studied (FIG. 14C). Two films containing $OD_{600}$=3/mL of empty chassis (no plasmid) or NB101 harboring the inducible CRISPRi components (pSC-LuxS1 and pdCas9ω) at early log phase ($OD_{600}$=0.2 before harvesting) were assembled on the biohybrid device, and the submerging culture media (20% LB) was collected for BB170 assay. Substantial inhibition of luxS solely from leaky expression was observed, judging from the fact that AI-2 activity of pSC-LuxS1 cultures was 3.4-fold lower than that of the empty chassis without any induction. However, this was also observed when cells were grown as liquid suspension cultures, and it's likely due to the intracellular peroxide generated from oxidative respiration. It was also noted that less significant AI-2 uptake of both cultures without the addition of glucose, especially the one harboring CRISPRi plasmids, within the observation window (2-8 h post-deposition). This was perhaps due to the altered growth when the cells were entrapped in film; also, since the intake of AI-2 creates a positive feedback loop from upregulating the lsr operon[13,14], the lower extracellular AI-2 levels of the CRISPRi cultures could impede its AI-2 uptake. Therefore, it was decided to omit adding extra glucose into our system in later experiments. It was then tested to see if CRISPRi of luxS could be regulated electronically. In FIG. 8B, the film (containing CRISPRi cells) subjected to electroinduction 3 hours after deposition consistently exhibited lower AI-2 activity compared to the uninduced control, proving controllable quenching of AI-2 QS through electrogenetics.

Having shown successful eCRISPRi of luxS, it was then decided to harness the multiplexed nature of CRISPR and combine CRISPRa of lasI and CRISPRi of luxS to create a 'bilingual' strain. Though many strategies for multiplexed gRNA expression have been previously explored[15], a method derived from the native CRISPR-Cas system was chosen. By flanking an array of gRNAs with 'direct repeats' (DR), which are repetitive sequences required for crRNA processing, the tandem gRNAs can be processed by RNase III in a tracrRNA-dependent manner, like how crRNAs are processed in Type II CRISPR systems[16-18]. Based on this approach, plasmid pSC-sg108+LuxS1 was constructed that comprised two key parts for inducible expression of multiple gRNAs: (1) gRNAs sg108 and LuxS1 were flanked with DR sequences and together were placed downstream of the oxyS promoter for peroxide-inducible control and (2) tracrRNA, required for gRNA processing, was individually expressed under a synthetic constitutive promoter. Next, pSC-sg108+LuxS1, with pdCas9ω and pMC-lasI-LAA were then transformed into NB101 cells to generate the 'bilingual' strain (FIG. 8C). To verify peroxide-induced, multiplexed CRISPRa/CRISPRi activity, the 'bilingual' cultures were grown in LB media at 30° C. and induced at $OD_{600}$=0.4 with 200 μM of peroxide. Elevated levels of AI-1 were found (FIG. 14D(i)) and reduced levels of AI-2 (FIG. 14D (ii)) in the induced samples compared to the uninduced control, confirming CRISPR-mediated activation and inhibition on both QS signal producers. Also noticed was the difference in autoinducer level between the control and experimental group were smaller when compared to the non-multiplex experiments in which only one gRNA was expressed. This was possibly a result of the changes in the stoichiometry of CRISPR components from reforming the architecture of the gRNA plasmid, as previous research had demonstrated that the balance between CRISPR components is crucial to achieve effective CRISPR transcription regulation. To overcome this, an attempt was made to induce the 'bilingual cells' multiple times at a fixed interval. Surprisingly, it was found that the cells that experienced more peroxide inductions displayed lower AI-2 activity (FIG. 14D(ii)). A complimentary upward trend for the AI-1 levels was not observed (FIG. 14D(i)), yet it was the sample induced twice (at hours 3 and 4) exhibited the highest AI-1 level. It was noted that unlike AI-2 inhibition which operates possibly on the timescale of gRNA transcription and processing, lasI upregulation required more time due to the need of translation and protein folding, contributing to the delay we observed in AI-1 levels. Nevertheless, these results demonstrated dynamic control of CRISPR transcription regulation, demonstrating that the peroxide-mediated CRISPR activity could be 'boosted' over time to reach the desired target response. Finally, to achieve electrogenetic multiplex CRISPR regulation, the 'bilingual' cells (final $OD_{600}$=5/mL) were assembled on the biohybrid device, and electrically-induced the 'biofilm' once at hour 0 or twice at hours 0 and 3 post-deposition (1800 s per induction). As shown in FIG. 8D, elevated AI-1 levels and diminished AI-2 activity were observed in both induced samples contrasted to the uninduced control. This also corroborated our 'bilingual' strain's capability of sending out different type of signals on cue, driving certain populations to elicit a biological response (e.g., bioluminescence). Moreover, of the two induced samples, the twice-induced 'biofilm' displayed higher AI-1 levels and lower AI-2 levels. This confirmed electrogenetic multiplexed CRISPR can also be dynamically regulated, thus providing another tunable parameter for this system. Overall, a 'bilingual' *E. coli* strain was engineered capable of switching its QS signaling to reach different audiences on electronic cue by simultaneously exerting both CRISPR activation and inhibition control over crucial components in QS systems.

Automated Dynamic Control of eCRISPRa Activity

Figure 9:
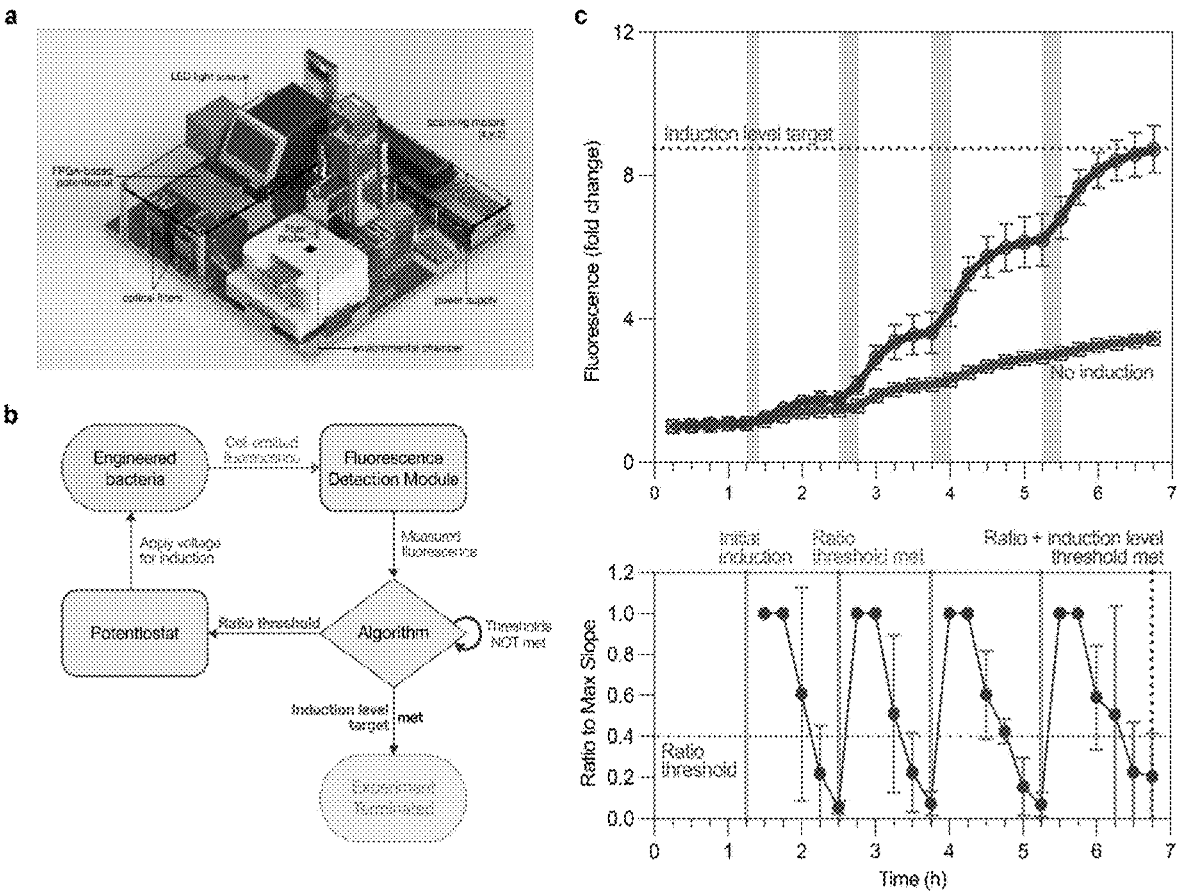
FIG. 9A-C. Autonomous dynamic control of gene expression via electrogenetic CRISPR (FIG. 9A) Schematic illustration of the Biospark system allowing real-time fluorescence measurements and electrochemical induction.

Inspired by the discovery of which of the oxyRS-based eCRISPR transcription regulation toolbox could be dynamically controlled, it was aimed to investigate and employ the temporal nature of this system to build a fully automated bioelectronic platform for electrogenetics control. First, a simpler construct (pOxy-sfGFP-AAV) was created that was stripped of the CRISPR components but retaining its ability to respond to peroxide, for studying the dynamics of the oxyRS induction system in suspension culture (FIG. 9). The experiment began by inducing these peroxide reporters with 0, 50, and 100 μM of peroxide and saw a sustained, upregulated response in both induced samples. Another dose of peroxide (50 or 100 μM) was then added to the previously induced sample. Consistent with the last cycle, both induced samples exhibited response above basal level in 15 minutes. An inducible behavior was observed in the first 30 minutes post-induction, however the difference in fluorescence response between all three samples quickly rendered indiscernible within 45 minutes. Similar behavior was seen when a third dose of peroxide was applied, proving peroxide induction is transient and can be administered repeatedly. Additionally, it was noticed that the response attenuated over time when the same amount of peroxide was added. It was hypothesized that this temporal behavior resulted mostly from the consumption of peroxide, and with a growing number of cells, a higher concentration of peroxide is required to maintain the molar ratio per cell to achieve a similar level of response.

Figure 16:
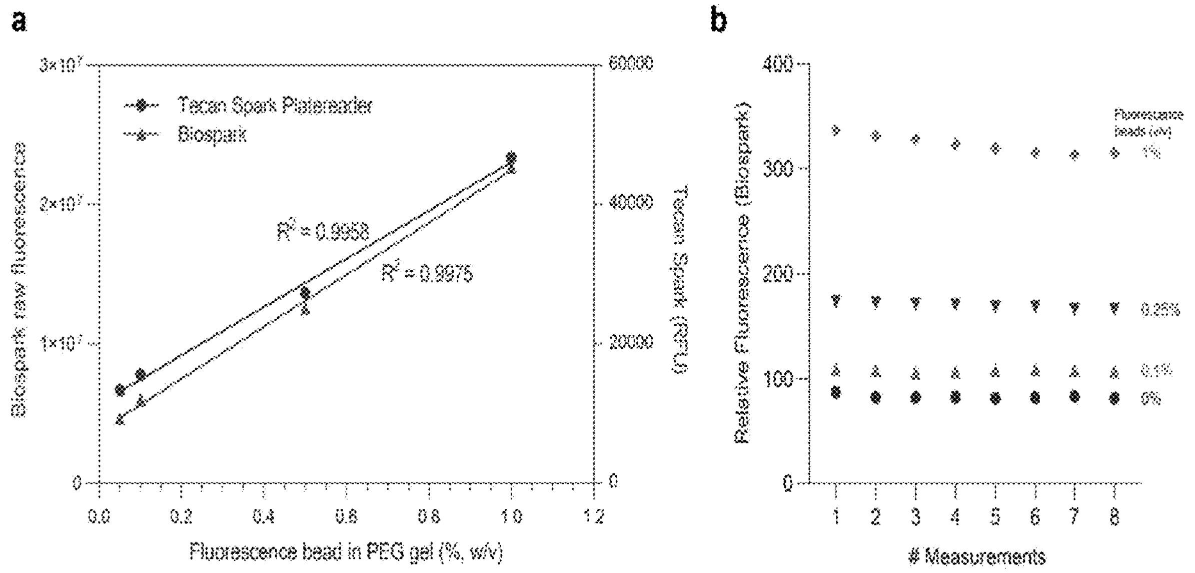
FIG. 16A-B. Performance in fluorescence measurements of the optical module from our custom Biospark System.
Figure 18:
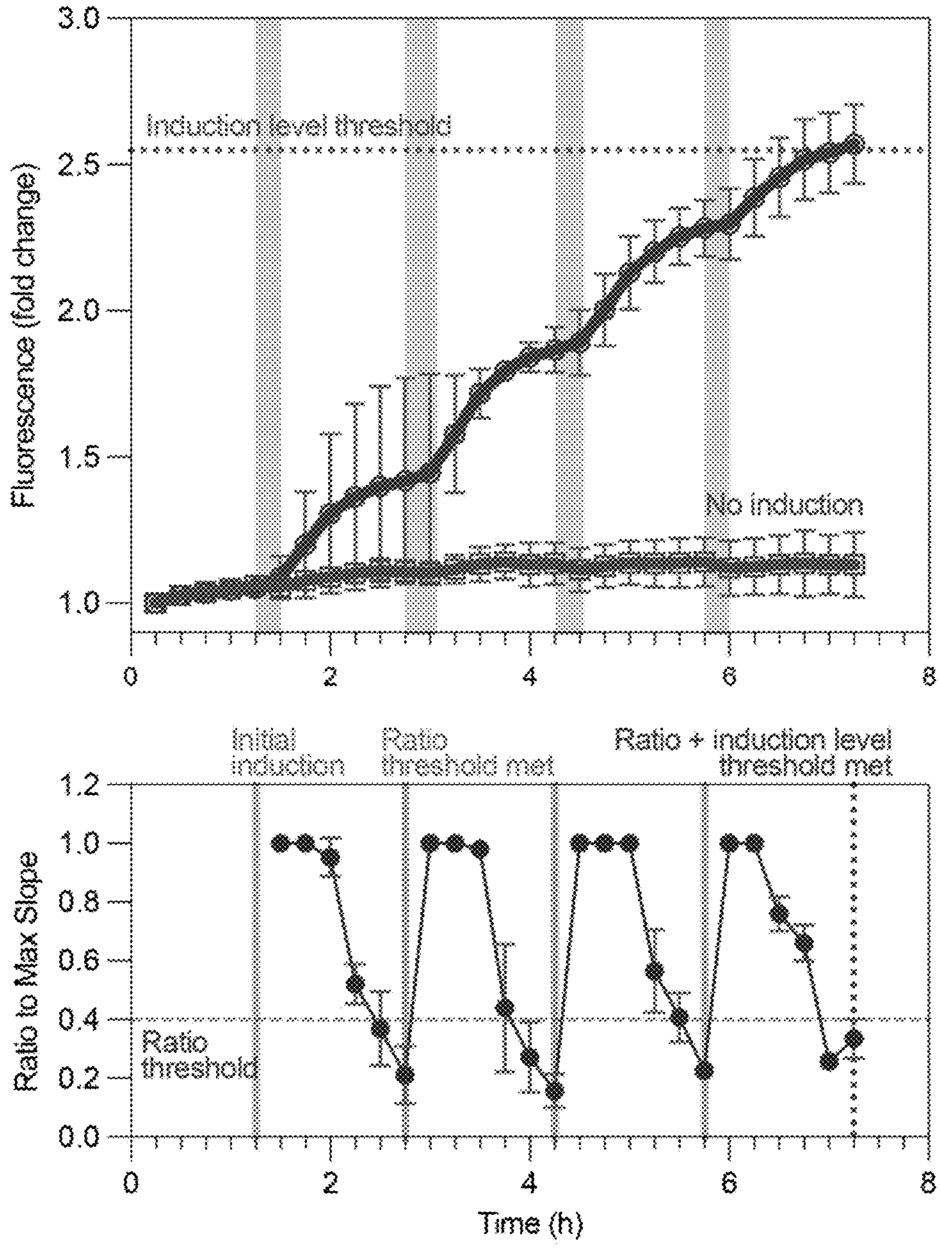
FIG. 18 Automated control of electro-induced gene expression. Autonomous dynamic control of gene expression via $H_2O_2$-inducible electro-induction. Top: fluorescence level of the artificial biofilm containing NB101 harboring plasmid pOxy-sfGFP. The experiment was automatically terminated when the fluorescence was over the induction level threshold. The fluorescence level of the negative control to which no induction voltage is applied is shown. The vertical zones indicate the periods when the induction voltage (−0.8 V) is applied. A total charge of 2 mC was applied to the cells in each zone. Bottom: Ratio to $S_{max}$ computed by custom algorithm. Ratio threshold was set at 0.4. The first vertical line indicates when the algorithm applied the initial induction voltage. Vertical lines indicate when two consecutive ratios were below set threshold, thus meeting the ratio threshold and triggering the potentiostat to apply induction voltage. The dotted vertical line indicates when both the ratio threshold and the induction level threshold were met, hence no voltage was applied, and the experiment ended. Error bars represent the standard deviation of individual replicates (n=2).

While electrogenetics provides an approach to seamlessly integrate signal transmission from electronic devices to biological systems, a pathway allowing communication from bio to electronics is also needed to form a closed network for fully automated control. Anoptical signaling (in our case, fluorescence) was chosen to bridge this gap since (1) fluorescence proteins have long been serving as proxy for gene expression[19,20], (2) fluorescence output allows for real-time measurements, and (3) optical signals are easily translated into electronic signal. Therefore, a bioelectronic system named 'Biospark' was constructed that consists of a fluorescence detection module for gene expression measurements, a built-in potentiostat for sending electronic commands, and a custom environmental chamber for cell culture (FIG. 9A). Metrics such as linearity, detection limit, and robustness of the fluorescence detection module in Biospark were all characterized and was on par with a commercial microplate reader (FIG. 16B). Next, multiple studies were carried out to study the expression dynamics driven by on-film, in situ electroinduction. First, cells were deposited that constitutively expressed GFP to track its growth curve (FIG. 17A). A "lag-phase" of approximately 1.25 hours was observed in which there was no increase in fluorescence detected, suggesting that there was no growth during this period. Henceforth, it was chosen to initiate electroinduction at 1.25 h after film deposition. Next, films containing peroxide reporters (pOxy-sGFP) were electrically induced for different durations. Similar characteristics were observed to that of suspension cultures: (1) regarding the dynamics, an initial surge in electro-induced gene expression was observed followed by quick deceleration to a plateau (FIG. 17B); (2) this system retained its inducibility, as shown by the increasing GFP levels when more charge was applied (FIG. 17C). Based on these findings, we built an algorithm for monitoring gene expression (FIG. 17D). In FIG. 9B, the automation workflow was illustrated: gene expression, as represented by GFP levels, was measured via the fluorescence detection module and transformed into a digital data to be fed into the custom algorithm. Two user-defined parameters in the algorithm, including the ratio threshold and expression level target, dictated when to 'boost' expression by electroinduction and when to terminate the experiment upon reaching the desired level of expression. Both peroxide reporters were then assembled (FIG. 18) and the cells carrying CRISPRa components (specifically, with pMC-GFP as the reporter plasmid) (FIG. 9C) into 'artificial biofilms' and controlled their expression with the automated bioelectronic system. In both cases, the algorithm effectively identified every 'plateaus' in the GFP expression profile and at each time signaled the potentiostat to apply charge (2 mC) for extra electroinduction. Cells were able to reach the target expression level after several inductions. It was noted that although a fixed charge was applied for every electroduction, this parameter could also serve as an orthogonal input to enable a more precise control. To summarize, the bioelectronic Biospark system endowed with the expression-tracking algorithm enabled autonomous, self-regulated control of electroinduced gene expression, including eCRISPR activity.

Network Integration for Remote, Feedback Control

By connecting everyday electronic devices to the internet and forming a collective network like the Internet of Things (IoT)[21], each member within can collect data and respond intelligently to users, thereby benefitting daily lives. The local bioelectronic device can be integrated into a network allowing multidirectional communication between 'living' systems, and realize remote or even remote feedback control of a dynamic biological system. FIG. 10A illustrates the full network, which is built upon the communication between (1) the local bioelectronic device, (2) the remote 'actuation checkpoint' enabled by a bio-electrochemical platform, and (3) users through the web and SMS (short message service). Instead of immediately sending a command to 'boost' expression when the local algorithm deemed a slump in GFP levels, this status is then wirelessly routed to the remote 'actuation checkpoint' to verify if additional electroinduction is needed. The 'actuation checkpoint' station is an algorithm-controlled, bio-electrochemical platform with the ability to 'write' and 'store' the generated information for documenting the number of times that electroinduction was administered. The platform consists of a patterned ITO electrode that is divided into two working electrodes and attached to a custom 3D-printed housing (FIG. 19A). Working electrode 1 (WE1) is tasked with generating peroxide as 'writing data' when receiving the signal from the local system, while working electrode 2 (WE2) is responsible for sensing the generated peroxide and record this information in the form of electric current. Specifically, a gelatin-based hydrogel containing horseradish peroxidase (HRP) was deposited on WE2 for peroxide measurements (FIG. 19C), as facilitated by the HRP-catalyzed enzymatic reaction and the following redox cycling with mediator FcN[7,22]. It was found that the endpoint current from WE2 increased each time a charge was applied on WE1 (FIG. 19D), even with long periods in between (FIG. 19E), confirming its ability to write, output, and store data. Controlled by a simple algorithm, the 'actuation checkpoint' then makes decisions based on the user-defined current threshold/target to either actuate the local potentiostat for electroinduction (via internet) or alert the user in real-time (via SMS) to terminate the experiment. To demonstrate a closed-loop feedback control, user-initiated termination will trigger photobleaching of the selected samples, as a representation of "destroying" the product expressed by the engineered bacteria. In FIG. 10B, successful network integration of a dynamic and complex biological system was shown, a robust bio-electrochemical platform, and user intervention allowing real-time communication to jointly regulate eCRISPR-mediated GFP expression.

In this work, a simple, controllable method was developed for assembling live cells into 'artificial biofilms' directly on the electrode to ensure efficient information flow at the bio-electronic interface and eliminate transport-limited heterogeneous responses in suspended biological systems[23,24]. This approach does not require genetic engineering; thus relieving the extra metabolic burden from the entrapped engineered cells for more effective use of resources on critical functions[25], or instead opening more possibility for immobilizing any living organisms without the need for inserting non-native genetic circuitries. Moreover, cell/PEG-SH co-deposition is shown to be scalable and spatially programmable, inviting future opportunities for cell grafting on complex formats like three-dimensional, miniaturized, arrayed electrodes; or on soft, flexible, bio-compatible materials, for wearable, ingestible or other portable system[26,27].

The repertoire of oxyRS-based electrogenetics was then expanded by engineering peroxide-mediated eCRISPR, enabling not only upregulation, but inhibition, and multiplexed control of a variety of genetic targets. These include two crucial QS-related genes that allow the relay of electrochemical signals to a broader yet selective audience of microbial populations through QS communication. Prevalent in nature, QS signaling is an ideal candidate for dispatching the highly-localized electrochemical cue to other ex situ biological populations with none or minimal genetic rewiring[9,28], and achieving coordination within a natural or synthetic consortium[4,29].

Next, the transient nature of oxyRS-based electrogenetics was studied and this feature was harnessed for dynamic control of eCRISPR activity. A first integrated electrogenetic system was presented, including both custom-made hardware and software, for fully automated control of eCRISPR-mediated expression. Here, biological responses were coupled with light to facilitate their transition into electronic signals in real time. Though noted that optogenetics, the use of light-sensitive proteins for regulation of various biological functions, has been a blooming field for interfacing biology and cybernetics[30,31], the disclosed multimodal approach that incorporated electrogenetics induction eliminated the need of an optical input in situations where light is not penetrable, such as commercial bioreactors with high-densities of cells. Furthermore, eCRISPR also provides one with an adaptable platform for simultaneous control of genes other than fluorescent proteins via multiplexed transcriptional regulation. It is also envisioned that the addition of artificial intelligence such as machine learning techniques for combining the data obtained in this study, for example, correlative dose-response relationships between charge inputs and outputs with gene expression, to generate an optimized model allowing smarter precision control.

Finally, the integration of bioelectronic systems with the internet was demonstrated to form a complete electrogenetic framework. By establishing this network of Bio-Nano Things, real-time, feedback control of eCRISPR activity was realized regardless of the constraint in physical distances. An immediate application of this framework would be for online monitoring and feedback control of cells inside bioreactors for smart biomanufacturing[32]. Nevertheless, since all electrogenetics components in this study (that is, peroxide signaling, CRISPR techniques, and QS communication) are either native to or can be easily ported to most biological systems, it is foreseen that the Bio-Nano Things network could be employed as the foundation of a plethora of intelligent systems or devices[33]. These include self-regulated, real-time reporting drug delivery biomedical devices for in situ production of a therapeutic[34,35], smart agriculture systems for monitored rhizosphere microbiome manipulation[36], or "sense-and-clean" strategies for battling environmental pollution to actively sense and remove contaminants[37], together serving as the blueprint for a more connected world in the future.

TABLE 1

Strains and plasmids used in this study.

Strains

| Name | Genotype | Reference |
|---|---|---|
| NEB10β | *E. coli* Δ(ara-leu) 7697 araD139 fhuA ΔlacX74 galK16 galE15 e14- ϕ80dlacZΔM15 recA1 relA1 endA1 nupG rpsL ($Str^R$) rph spoT1 Δ(mrr-hsdRMS-mcrBC) | New England Biolabs |
| DH5α-sfGFP | *E. coli* DH5α attTn7::mTn7ΦsfGFP | This study |
| NB101 | *E. coli* ZK126 ΔrpoZ | Bhokisham et al.[2] |
| JLD271 | *E. coli* K-12 ΔlacX74 sdiA271::Cam | Lindsay et al.[38] |
| BB170 | *V. harveyi* luxN::Tn5 | Surrette et al.[11] |

Plasmids

| Name | Description | Reference |
|---|---|---|
| pSC-S108gRNA | pSC101 ori, $Kan^r$, soxR, soxRSp, spacer 108, gRNA scaffold | Bhokisham et al.[2] |
| pOxy-LacZ-laa | | Terrell et al.[3] |
| pSC-O108 | pSC101 ori, $Kan^r$, proD promoter, RBS31, oxyR, oxySp, spacer 108, gRNA scaffold | This study |
| pdCas9ω | ω was inserted into C termini of dCas9 in pdCas9-bacteria (Addgene plasmid # 44249), p15A ori, pLtetO-1, $Cm^r$ | Bhokisham et al.[2] |
| pMC-GFP | pWJ89 with pBR322 and $Amp^r$ instead of pSC101 ori and $Kan^r$ | Bhokisham et al.[2] |
| pMC-lasI-LAA | pMC-GFP lasI with the LAA ssRA tag instead of gfpmut2 | This study |
| pLasR_S129T-GFPmut3 | ***Check*** | |
| pS1gRNA | soxS specific gRNA spacers S1 inserted into pgRNAbacteria (Addgene plasmid # 44251) with pBR322 ori, $Amp^r$, BBa_J23119 promoter | Bhokisham et al.[2] |
| pControlgRNA | Control spacer (from Bikard et al.[39]) in pgRNA-bacteria (Addgene plasmid # 44251) with pBR322 origin, $Amp^r$, J23119 promoter | Bhokisham et al.[2] |

TABLE 1-continued

| Strains and plasmids used in this study. | | |
|---|---|---|
| pLuxS1 | pS1gRNA with luxS specific gRNA spacer LuxS1 instead of S1 | This study |
| pSC-LuxS1 | pSC-O108 with luxS specific gRNA spacer LuxS1 instead of 108 | This study |
| pSC-sg108 + LuxS1 | pSC101 ori, $Kan^r$, BBa_J23100 promoter, tracrRNA, b1002 terminator, proD promoter, RBS 31, oxyR, oxyRS promoter, DR, spacer 108, DR, spacer LuxS1, DR, b1006 terminator | This study |
| pOxy-sGFP | pBR322 ori, $Amp^r$, proD promoter, RBS 31, oxyR, oxyRS promoter, RBS 33, sfGFP | Li, Wang et al.[24] |
| pOxy-sfGFP-AAV | AAV ssRA tag inserted to sfGFP in pOxy-sfGFP | This study |

TABLE 2

Sequences of relevant genetic parts

| Name | Sequence (5'-3') |
|---|---|
| proD promoter | AAAGTTAAACAAAATTATTTGTAGAGGGAAACCGTTGTGGTCTCCCTGAATATATTATACGAGCCTT<br>ATGCATGCCCGTAAAGTTATCCAGCAACCACTCATAGACCTAGGGCAGCAGATAGGGACGACGTG<br>GTGTTAGCTGTG |
| oxyR | ATGAATATTCGTGATCTTGAGTACCTGGTGGCATTGGCTGAACACCGCCATTTTCGGCGTGCGGCA<br>GATTCCTGCCACGTTAGCCAGCCGACGCTTAGCGGGCAAATTCGTAAGCTGGAAGATGAGCTGGG<br>CGTGATGTTGCTGGAGCGGACCAGCCGTAAAGTGTTGTTCACCCAGGCGGGAATGCTGCTGGTGG<br>ATCAGGCGCGTACCGTGCTGCGTGAGGTGAAAGTCCTTAAAGAGATGGCAAGCCAGCAGGGCGA<br>GACGATGTCCGGACCGCTGCACATTGGTTTGATTCCCACAGTTGGACCGTACCTGCTACCGCATATT<br>ATCCCTATGCTGCACCAGACCTTTCCAAAGCTGGAAATGTATCTGCATGAAGCACAGACCCACCAGT<br>TACTGGCGCAACTGGACAGCGGCAAACTCGATTGCGTGATCCTCGCGCTGGTGAAAGAGAGCGAA<br>GCATTCATTGAAGTGCCGTTGTTTGATGAGCCAATGTTGCTGGCTATCTATGAAGATCACCCGTGG<br>GCGAACCGCGAATGCGTACCGATGGCCGATCTGGCAGGGGAAAAACTGCTGATGCTGGAAGATG<br>GTCACTGTTTGCGCGATCAGGCAATGGGTTTCTGTTTTGAAGCCGGGGCGGATGAAGATACACACT<br>TCCGCGCGACCAGCCTGGAAACTCTGCGCAACATGGTGGCGGCAGGTAGCGGGATCACTTTACTG<br>CCAGCGCTGGCTGTGCCGCCGGAGCGCAAACGCGATGGGGTTGTTTATCTGCCGTGCATTAAGCC<br>GGAACCACGCCGCACTATTGGCCTGGTTTATCGTCCTGGCTCACCGCTGCGCAGCCGCTATGAGCA<br>GCTGGCAGAGGCCATCCGCGCAAGAATGGATGGCCATTTCGATAAAGTTTTAAAACAGGCGGTTT<br>AA |
| RBS BBa_B0031 | TCACACAGGAAACC |
| oxyS promoter | TATCCATCCTCCATCGCCACGATAGTTCATGGCGATAGGTAGAATAGCAATGAACGATTATCCCTAT<br>CAAGCATTCTGACTGATAATTGCTCACA |
| Spacer 108 | GCGTGTTGTGGAAGATCCGGCCTGCAGCCA |
| gRNA scaffold | GTTTTAGAGCTAGAAATAGCAAGTTAAAATAAGGCTAGTCCGTTATCAACTTGAAAAAGTGGCACC<br>GAGTCGGTGC |
| GFPmut2 | ATGAGTAAAGGAGAAGAACTTTTCACTGGAGTTGTCCCAATTCTTGTTGAATTAGATGGTGATGTT<br>AATGGGCACAAATTTTCTGTCAGTGGAGAGGGTGAAGGTGATGCAACATACGGAAAACTTACCCTT<br>AAATTTATTTGCACTACTGGAAAACTACCTGTTCCATGGCCAACACTTGTCACTACTTTCGCGTATGG<br>TCTTCAATGCTTTGCGAGATACCCAGATCATATGAAACAGCATGACTTTTTCAAGAGTGCCATGCCC<br>GAAGGTTATGTACAGGAAAGAACTATATTTTTCAAAGATGACGGGAACTACAAGACACGTGCTGA<br>AGTCAAGTTTGAAGGTGATACCCTTGTTAATAGAATCGAGTTAAAAGGTATTGATTTTAAAGAAGA<br>TGGAAACATTCTTGGACACAAATTGGAATACAACTATAACTCACACAATGTATACATCATGGCAGA<br>CAAACAAAAGAATGGAATCAAAGTTAACTTCAAAATTAGACACAACATTGAAGATGGAAGCGTTCA<br>ACTAGCAGACCATTATCAACAAAATACTCCAATTGGCGATGGCCCTGTCCTTTTACCAGACAACCAT<br>TACCTGTCCACACAATCTGCCCTTTCGAAAGATCCCAACGAAAAGAGAGACCACATGATCCTTCTTG<br>AGTTTGTAACAGCTGCTGGGATTACACATGGCATGGATGAACTATACAAA |
| lasI-LAA | ATGATCGTACAAATTGGTCGGCGCGAAGAGTTCGATAAAAAACTGCTGGGCGAGATGCACAAGTT<br>GCGTGCTCAAGTGTTCAAGGAGCGCAAAGGCTGGGACGTTAGTGTCATCGACGAGATGGAAATCG<br>ATGGTTATGACGCACTCAGTCCTTATTACATGTTGATCCAGGAAGATACTCCTGAAGCCCAGGTTTT<br>CGGTTGCTGGCGAATTCTCGATACCACTGGCCCCTACATGCTGAAGAACACCTTCCCGGAGCTTCTG<br>CACGGCAAGGAAGCGCCTTGCTCGCCGCACATCTGGGAACTCAGCCGTTTCGCCATCAACTCTGGA<br>CAGAAAGGCTCGCTGGGCTTTTCCGACTGTACGCTGGAGGCGATGCGCGCGCTGGCCCGCTACAG<br>CCTGCAGAACGACATCCAGACGCTGGTGACGGTAACCACCGTAGGCGTGGAGAAGATGATGATCC<br>GTGCCGGCCTGGACGTATCGCGCTTCGGTCCGCACCTGAAGATCGGCATCGAGCGCGCGGTGGCC<br>TTGCGCATCGAACTCAATGCCAAGACCCAGATCGCGCTTTACGGGGGAGTGCTGGTGGAACAGCG<br>ACTGGCGGTTTCAGCAGCGAACGACGAAAATTACGCCCTTGCAGCGTGATAATAA |
| LasR (S129T) | |
| Spacer LuxS1 | GGTATGATCGACTGTGAAGCTATCTAACAA |
| Spacer Control | TGAGACCAGTCTCGGAAGCTCAAAGGTCTC |

TABLE 2-continued

Sequences of relevant genetic parts

| Name | Sequence (5'-3') |
| --- | --- |
| crRNAs 108, LuxS1, and terminator BBa_b0016 | CTCGAGGTTTTAGAGCTATGCTGTTTTGAATGGTCCCAAAACGCGTGTTGTGGAAGATCCGGCCTG CAGCCAGTTTTAGAGCTATGCTGTTTTGAATGGTCCCAAAACGGTATGATCGACTGTGAAGCTATCT AACAAGTTTTAGAGCTATGCTGTTTTGAATGGTCCCAAAACAAAAAAAAACCCCGCCCCTGACAGG GCGGGGTTTTTTTTGGATCC |
| Promoter BBa_J23100, tracrRNA, and terminator BBa_b1002 | AAGCTTTTGACGGCTAGCTCAGTCCTAGGTACAGTGCTAGCGGAACCATTCAAAACAGCATAGCAA GTTAAAATAAGGCTAGTCCGTTATCAACTTGAAAAAGTGGCACCGAGTCGGTGCTTTTTTTCGCAAA AAACCCCGCTTCGGCGGGGTTTTTTCGCGACGTC |
| sfGFP-AAV | |

TABLE 3

Primers used in this study.

| Name | Sequence (5'-3') |
| --- | --- |
| SW01 | TGTTTGACAGCTTATCATC |
| SW02 | GCGTCCGGCGTAGAGTCGTGTGAGCAATTATCAG |
| SW03 | CACACGAGCGTGTTGTGG |
| SW04 | GTAGAGAAAAAAGCACCGACTCGG |
| SW05 | GTCGGTGCTTTTTTCTCTACCTCTACGCCGGACGCATC |
| SW06 | TTCCACAACACGCTCGTGTGTCGTGTGAGCAATTATCAGTCAG |
| SW07 | |
| SW08 | |
| SW09 | CTAACGGATCCGCTTTTTTCTCTACCTCTACGCC |
| SW10 | CTAAGCTCGAGTGTGAGCAATTATCAGTCAGAATG |
| SW11 | |
| SW12 | |
| SW13 | GGATCCCATGGTACGCGTG |
| SW14 | CTAGATTTCTCCTCTTTAAAGGAATTCGC |
| SW15 | TTTAAAGAGGAGAAATCTAGATGATCGTACAAATTGGTCGG |
| SW16 | GCACGCGTACCATGGGATCCTTATTATCACGCTGCAAGGG |
| SW17 | |
| SW18 | |

REFERENCES

The following are hereby incorporated by reference herein in their entirety.

1 Tschirhart, T. et al. Electronic control of gene expression and cell behaviour in *Escherichia coli* through redox signalling. *Nat Commun* 8, 14030, doi:10.1038/ncomms14030 (2017).

2 Bhokisham, N. et al. A redox-based electrogenetic CRISPR system to connect with and control biological information networks. *Nat Commun* 11, 2427, doi:10.1038/s41467-020-16249-x (2020).

3 Terrell, J. L. et al. Bioelectronic control of a microbial community using surface-assembled electrogenetic cells to route signals. *Nat Nanotechnol* 16, 688-697, doi:10.1038/s41565-021-00878-4 (2021).

4 Stephens, K., Zakaria, F. R., VanArsdale, E., Payne, G. F. & Bentley, W. E. Electronic signals are electrogenetically relayed to control cell growth and co-culture composition. *Metab Eng Commun* 13, e00176, doi:10.1016/j.mec.2021.e00176 (2021).

5 Kim, E. et al. Redox Is a Global Biodevice Information Processing Modality. *Proceedings of the IEEE* 107, 1402-1424, doi:10.1109/JPROC.2019.2908582 (2019).

6 VanArsdale, E., Pitzer, J., Payne, G. F. & Bentley, W. E. Redox Electrochemistry to Interrogate and Control Biomolecular Communication. *iScience* 23, 101545, doi:10.1016/j.isci.2020.101545 (2020).

7 Li, J. et al. Mediated Electrochemistry to Mimic Biology's Oxidative Assembly of Functional Matrices. *Advanced Functional Materials* 30, 2001776, doi:https://doi.org/10.1002/adfm.202001776 (2020).

8 Sultana, S. T. et al. Electrochemical scaffold generates localized, low concentration of hydrogen peroxide that inhibits bacterial pathogens and biofilms. *Sci Rep* 5, 14908, doi:10.1038/srep14908 (2015).

9 Wang, S., Payne, G. F. & Bentley, W. E. Quorum Sensing Communication: Molecularly Connecting Cells, Their Neighbors, and Even Devices. *Annu Rev Chem Biomol Eng* 11, 447-468, doi:10.1146/annurev-chembioeng-101519-124728 (2020).

10 Wang, S., Payne, G. F. & Bentley, W. E. Quorum sensing componentry opens new lines of communication. *EMBO J* 41, e112162, doi:10.15252/embj.2022112162 (2022).

11 Surette, M. G., Miller, M. B. & Bassler, B. L. Quorum sensing in *Escherichia coli, Salmonella typhimurium*, and *Vibrio harveyi*: a new family of genes responsible for autoinducer production. *Proc Natl Acad Sci USA* 96, 1639-1644, doi:10.1073/pnas.96.4.1639 (1999).

12 Wang, L., Hashimoto, Y., Tsao, C. Y., Valdes, J. J. & Bentley, W. E. Cyclic AMP (cAMP) and cAMP receptor protein influence both synthesis and uptake of extracellular autoinducer 2 in *Escherichia coli. J Bacteriol* 187, 2066-2076, doi:10.1128/JB.187.6.2066-2076.2005 (2005).

13 Quan, D. N., Tsao, C. Y., Wu, H. C. & Bentley, W. E. Quorum Sensing Desynchronization Leads to Bimodality and Patterned Behaviors. *PLoS Comput Biol* 12, e1004781, doi:10.1371/journal.pcbi.1004781 (2016).

14 Xavier, K. B. & Bassler, B. L. Regulation of uptake and processing of the quorum-sensing autoinducer AI-2 in *Escherichia coli. J Bacteriol* 187, 238-248, doi:10.1128/JB.187.1.238-248.2005 (2005).

15 McCarty, N. S., Graham, A. E., Studena, L. & Ledesma-Amaro, R. Multiplexed CRISPR technologies for gene editing and transcriptional regulation. *Nat Commun* 11, 1281, doi:10.1038/s41467-020-15053-x (2020).

16 Liao, C. et al. Modular one-pot assembly of CRISPR arrays enables library generation and reveals factors influencing crRNA biogenesis. *Nat Commun* 10, 2948, doi:10.1038/s41467-019-10747-3 (2019).

17 Barrangou, R. et al. CRISPR provides acquired resistance against viruses in prokaryotes. *Science* 315, 1709-1712, doi:10.1126/science.1138140 (2007).

18 Deltcheva, E. et al. CRISPR RNA maturation by trans-encoded small RNA and host factor RNase III. *Nature* 471, 602-607, doi:10.1038/nature09886 (2011).

19 Chalfie, M., Tu, Y., Euskirchen, G., Ward, W. W. & Prasher, D. C. Green fluorescent protein as a marker for gene expression. *Science* 263, 802-805, doi:10.1126/science.8303295 (1994).

20 March, J. C., Rao, G. & Bentley, W. E. Biotechnological applications of green fluorescent protein. *Appl Microbiol Biotechnol* 62, 303-315, doi: 10.1007/s00253-003-1339-y (2003).

21 Kumar, S., Tiwari, P. & Zymbler, M. Internet of Things is a revolutionary approach for future technology enhancement: a review. *Journal of Big Data* 6, 111, doi:10.1186/s40537-019-0268-2 (2019).

22 Motabar, D. et al. Simple, rapidly electroassembled thiolated PEG-based sensor interfaces enable rapid interrogation of antibody titer and glycosylation. *Biotechnol Bioeng* 118, 2744-2758, doi:10.1002/bit.27793 (2021).

23 VanArsdale, E. et al. Electrogenetic Signal Transmission and Propagation in Coculture to Guide Production of a Small Molecule, Tyrosine. *ACS Synth Biol* 11, 877-887, doi:10.1021/acssynbio.1c00522 (2022).

24 Li, J. et al. Interactive Materials for Bidirectional Redox-Based Communication. *Advanced Materials* 33, 2007758, doi:https://doi.org/10.1002/adma.202007758 (2021).

25 Wu, G. et al. Metabolic Burden: Cornerstones in Synthetic Biology and Metabolic Engineering Applications. *Trends Biotechnol* 34, 652-664, doi:10.1016/j.tibtech.2016.02.010 (2016).

26 Shang, W. et al. Selective assembly and functionalization of miniaturized redox capacitor inside microdevices for microbial toxin and mammalian cell cytotoxicity analyses. *Lab Chip* 18, 3578-3587, doi:10.1039/c81c00583d (2018).

27 Shin, M., Lim, J., An, J., Yoon, J. & Choi, J. W. Nanomaterial-based biohybrid hydrogel in bioelectronics. *Nano Converg* 10, 8, doi:10.1186/s40580-023-00357-7 (2023).

28 Wang, S., Payne, G. F. & Bentley, W. E. in *Gene Expression and Control* (ed Uchiumi Fumiaki) Ch. 9 (IntechOpen, 2018).

29 VanArsdale, E. et al. Electrogenetic signaling and information propagation for controlling microbial consortia via programmed lysis. *Biotechnol Bioeng*, doi:10.1002/bit.28337 (2023).

30 Milias-Argeitis, A., Rullan, M., Aoki, S. K., Buchmann, P. & Khammash, M. Automated optogenetic feedback control for precise and robust regulation of gene expression and cell growth. *Nat Commun* 7, 12546, doi:10.1038/ncomms12546 (2016).

31 Mansouri, M. et al. Smart-watch-programmed green-light-operated percutaneous control of therapeutic transgenes. *Nat Commun* 12, 3388, doi:10.1038/s41467-021-23572-4 (2021).

32 Gargalo, C. L. et al. Towards smart biomanufacturing: a perspective on recent developments in industrial measurement and monitoring technologies for bio-based production processes. *J Ind Microbiol Biotechnol* 47, 947-964, doi:10.1007/s10295-020-02308-1 (2020).

33 Akyildiz, I. F., Pierobon, M., Balasubramaniam, S. & Koucheryavy, Y. The internet of Bio-Nano things. *IEEE Communications Magazine* 53, 32-40, doi:10.1109/MCOM.2015.7060516 (2015).

34 Krawczyk, K. et al. Electrogenetic cellular insulin release for real-time glycemic control in type 1 diabetic mice. *Science* 368, 993-1001, doi:10.1126/science.aau7187 (2020).

35 Senturk, S., Kok, I. & Sentürk, F. Internet of Nano, Bio-Nano, Biodegradable and Ingestible Things: A Survey. ArXiv abs/2202.12409 (2022).

36 Afridi, M. S. et al. Harnessing microbial multitrophic interactions for rhizosphere microbiome engineering. *Microbiol Res* 265, 127199, doi:10.1016/j.micres.2022.127199 (2022).

37 Atkinson, J. T. et al. Real-time bioelectronic sensing of environmental contaminants. *Nature* 611, 548-553, doi:10.1038/s41586-022-05356-y (2022).

38 Lindsay, A. & Ahmer, B. M. Effect of sdiA on biosensors of N-acylhomoserine lactones. *J Bacteriol* 187, 5054-5058, doi:10.1128/JB.187.14.5054-5058.2005 (2005).

39 Bikard, D. et al. Programmable repression and activation of bacterial gene expression using an engineered CRISPR-Cas system. *Nucleic Acids Res* 41, 7429-7437, doi:10.1093/nar/gkt520 (2013).

What is claimed is:

1. A control system comprising:

an apparatus configured to electrically induce gene expression;

a detection system configured to detect level of the gene expression in the apparatus, the detection system configured to provide electrical signals indicative of the level of gene expression; and a computing device configured to implement closed loop control of the level of gene expression in the apparatus based on the electrical signals, wherein the computing device controls voltages applied by the apparatus to electrically induce the gene expression, and wherein the gene expression results in fluorescence, and wherein the detection system is a fluorescence detection system that provides fluorescence measurements, and wherein the closed loop control comprises:

computing a slope as a difference between two consecutive fluorescence measurements;

accessing a stored maximum slope value;

computing a ratio of the slope to the maximum slope value; and controlling, based on at least the ratio, the voltages applied by the apparatus.

2. The control system of claim 1, wherein the apparatus comprises a potentiostat configured to apply the voltages to electrically induce the gene expression.

3. The control system of claim 2, wherein the apparatus comprises a plurality of wells, wherein the potentiostat includes a reference electrode, a counter electrode, and a plurality of working electrodes, and wherein each well of the plurality of wells comprises a working electrode of the plurality of working electrodes.

* * * * *